United States Patent [19]

Sircom et al.

[11] Patent Number: 5,322,517
[45] Date of Patent: Jun. 21, 1994

[54] DISPOSABLE AUTOMATIC HYPODERMIC NEEDLE GUARD

[75] Inventors: Richard C. Sircom, Dartmouth; Yousef M. Youssef; Robert S. Solomon, both of Ottawa, all of Canada

[73] Assignee: Sero-Guard Corporation, Ottawa, Canada

[21] Appl. No.: 730,920

[22] PCT Filed: Feb. 1, 1990

[86] PCT No.: PCT/CA90/00031
§ 371 Date: Oct. 1, 1991
§ 102(e) Date: Oct. 1, 1991

[87] PCT Pub. No.: WO90/08564
PCT Pub. Date: Aug. 9, 1990

Related U.S. Application Data

[63] Continuation-in-part of Ser. No. 309,305, Feb. 1, 1989, abandoned.

[51] Int. Cl.[5] .............................................. A61M 5/32
[52] U.S. Cl. ...................................... 604/198; 604/263
[58] Field of Search ............... 604/110, 192, 197, 198, 604/263

[56] References Cited
U.S. PATENT DOCUMENTS

| 4,778,453 | 10/1988 | Lopez | 604/110 |
|---|---|---|---|
| 4,781,692 | 11/1988 | Jagger et al. | 604/171 |
| 4,795,432 | 1/1989 | Karczmer | 604/110 |
| 4,795,443 | 1/1989 | Permenter et al. | 604/198 |
| 4,863,434 | 9/1989 | Bayless | 604/198 |
| 4,863,435 | 9/1989 | Sturman et al. | 604/198 |
| 4,863,436 | 9/1989 | Glick | 604/198 |
| 4,887,998 | 12/1989 | Martin et al. | 604/198 |
| 4,917,672 | 4/1990 | Terndrup et al. | 604/192 |
| 4,929,241 | 5/1990 | Kulli | 604/263 |

FOREIGN PATENT DOCUMENTS

| 352928 | 1/1990 | European Pat. Off. |
| 2586568 | 9/1985 | France . |
| 2178322 | 2/1987 | United Kingdom . |
| 8910767 | 11/1989 | World Int. Prop. O. |
| 9101151 | 2/1991 | World Int. Prop. O. |

Primary Examiner—C. Fred Rosenbaum
Assistant Examiner—Michael Rafa
Attorney, Agent, or Firm—David J. French

[57] ABSTRACT

A needle tip protecting device is provided for hypodermic needles, catheters, and the like. The device is small enough to be stored at the base of the needle prior to and during use. After use it may be slid to cover the needle tip where it automatically self-attaches and becomes non-removable. Various embodiments of mechanisms to achieve this effect are described.

15 Claims, 25 Drawing Sheets

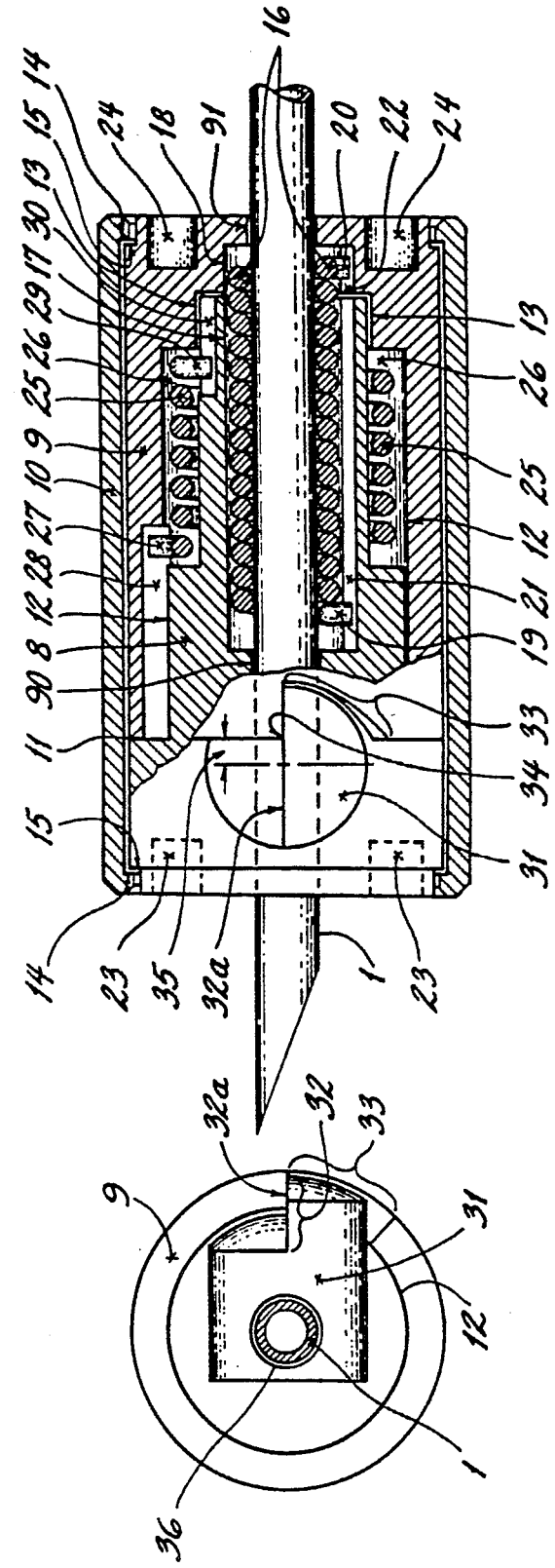

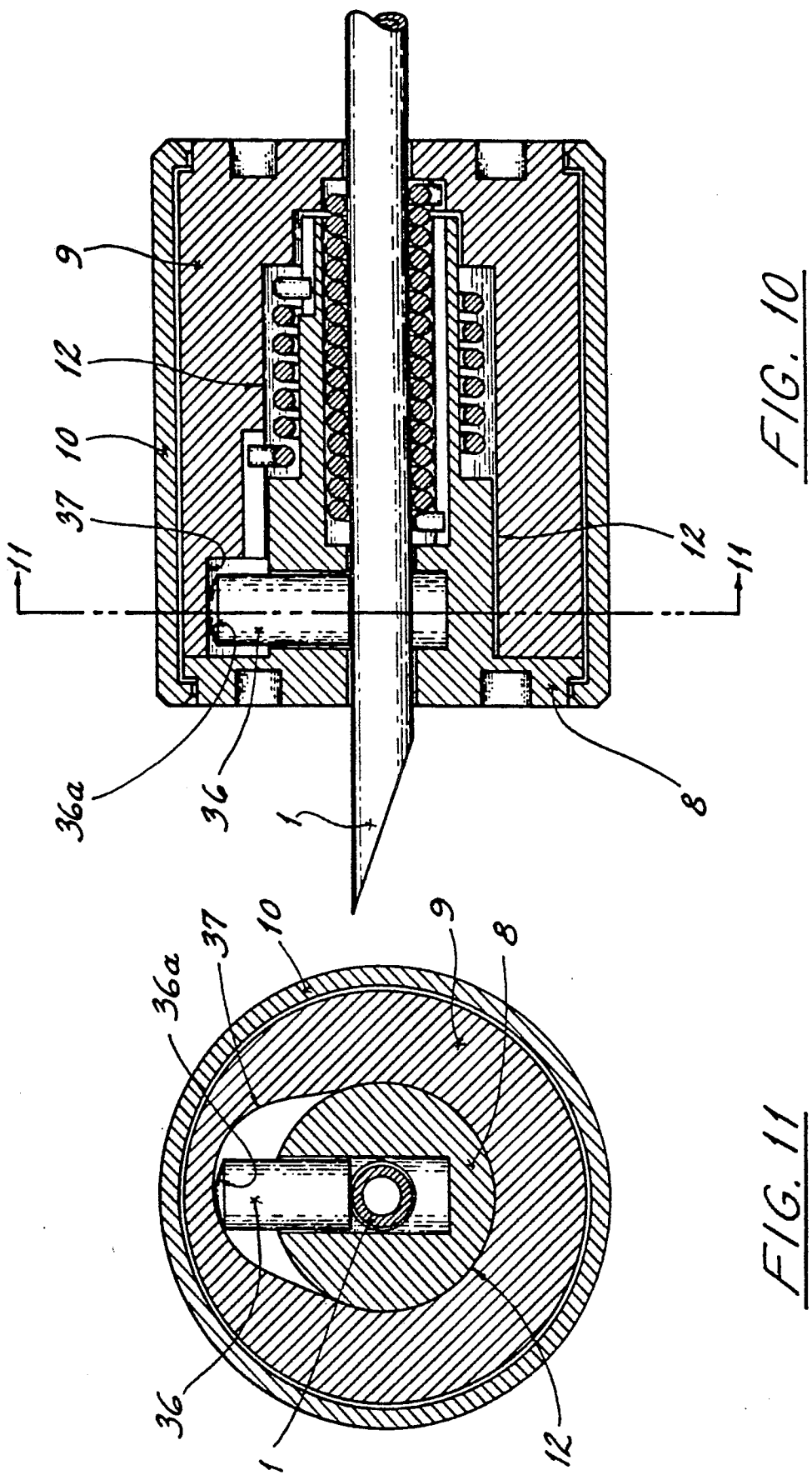

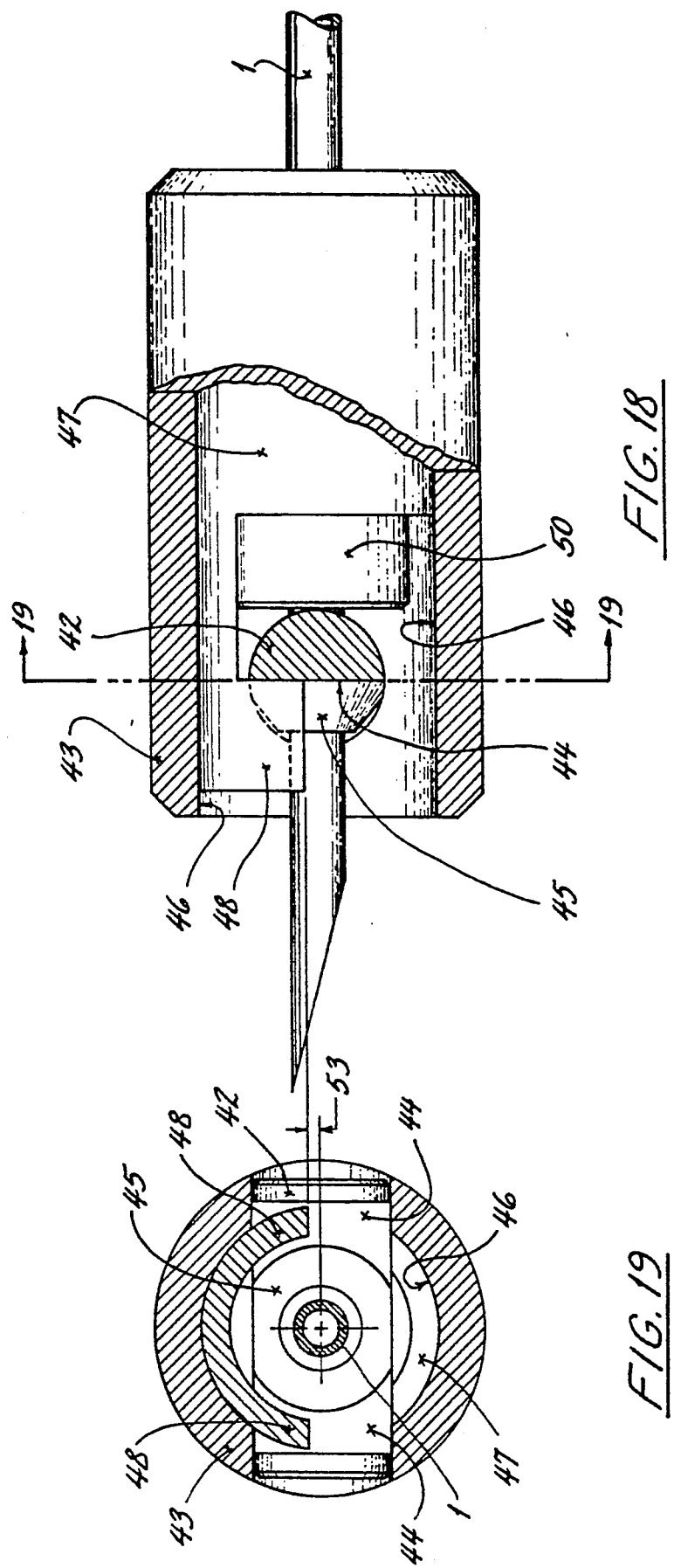

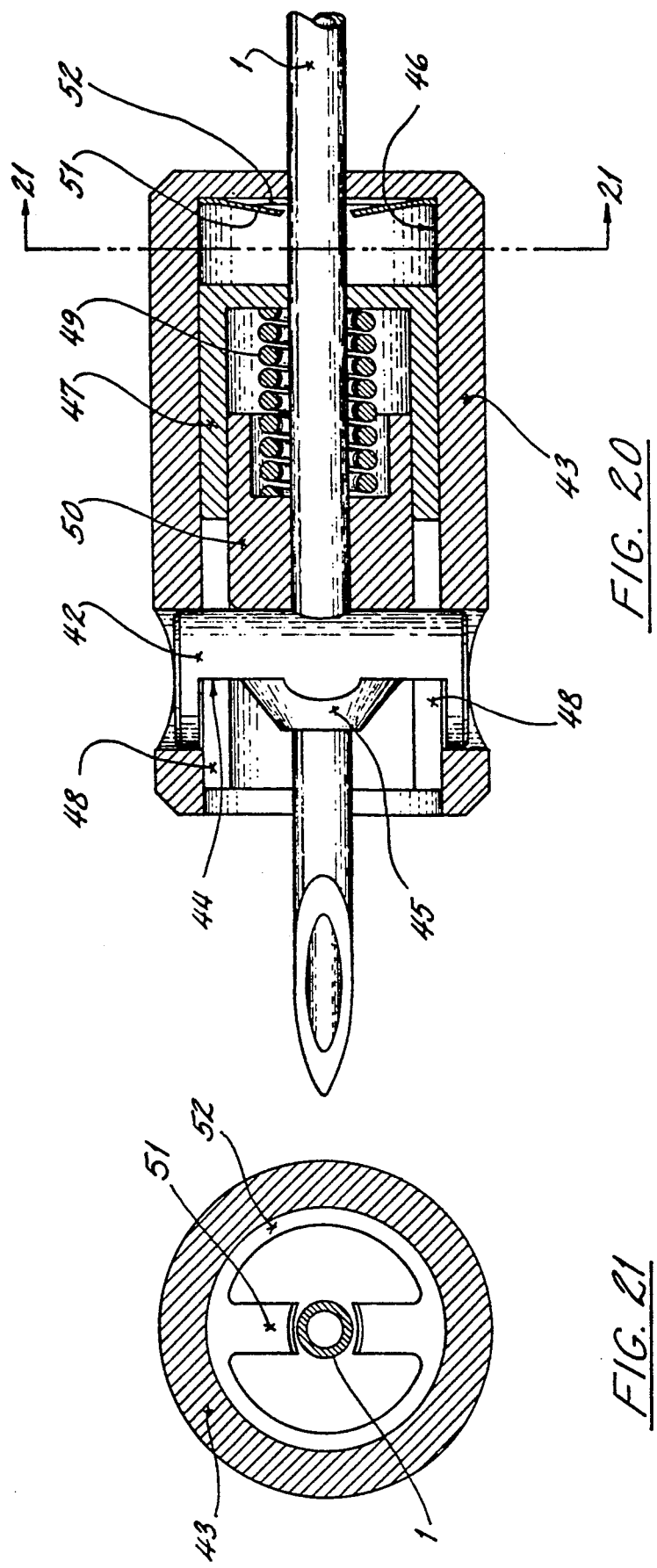

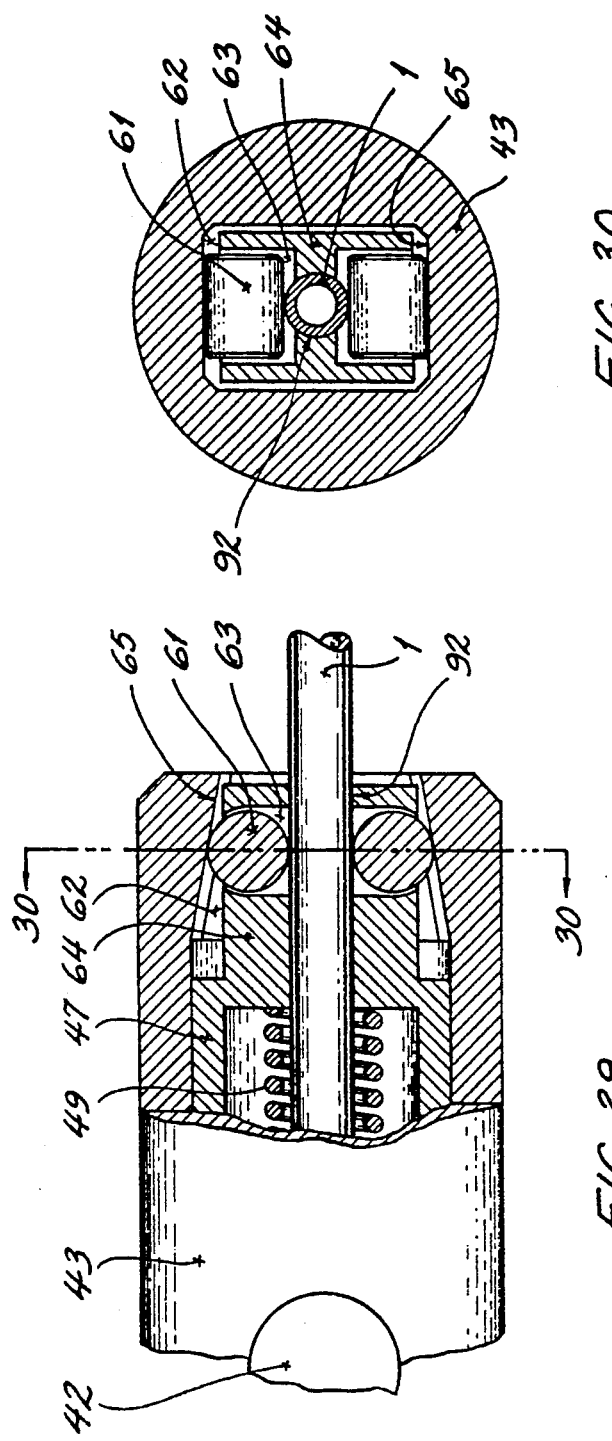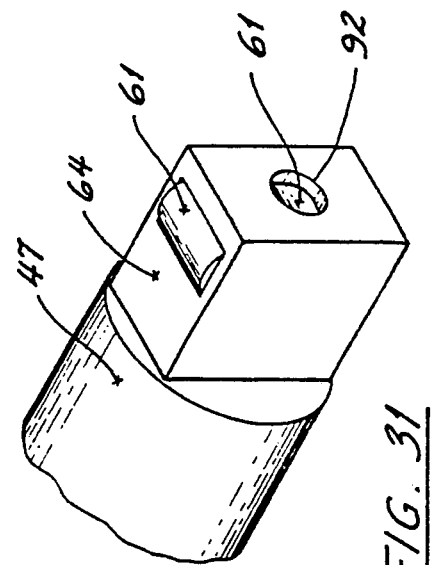

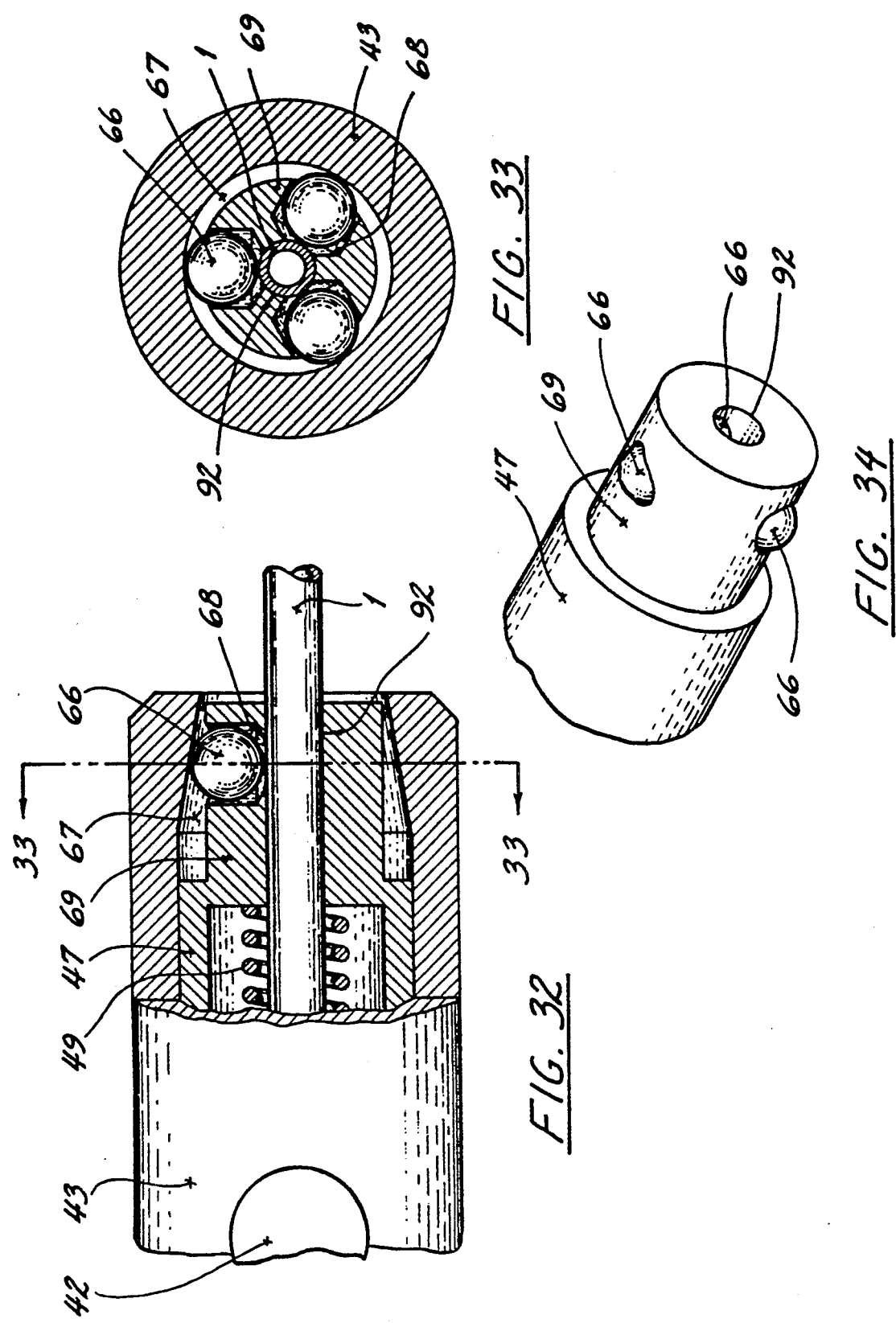

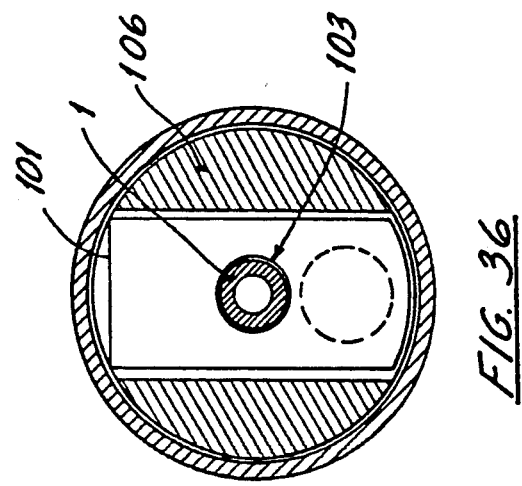
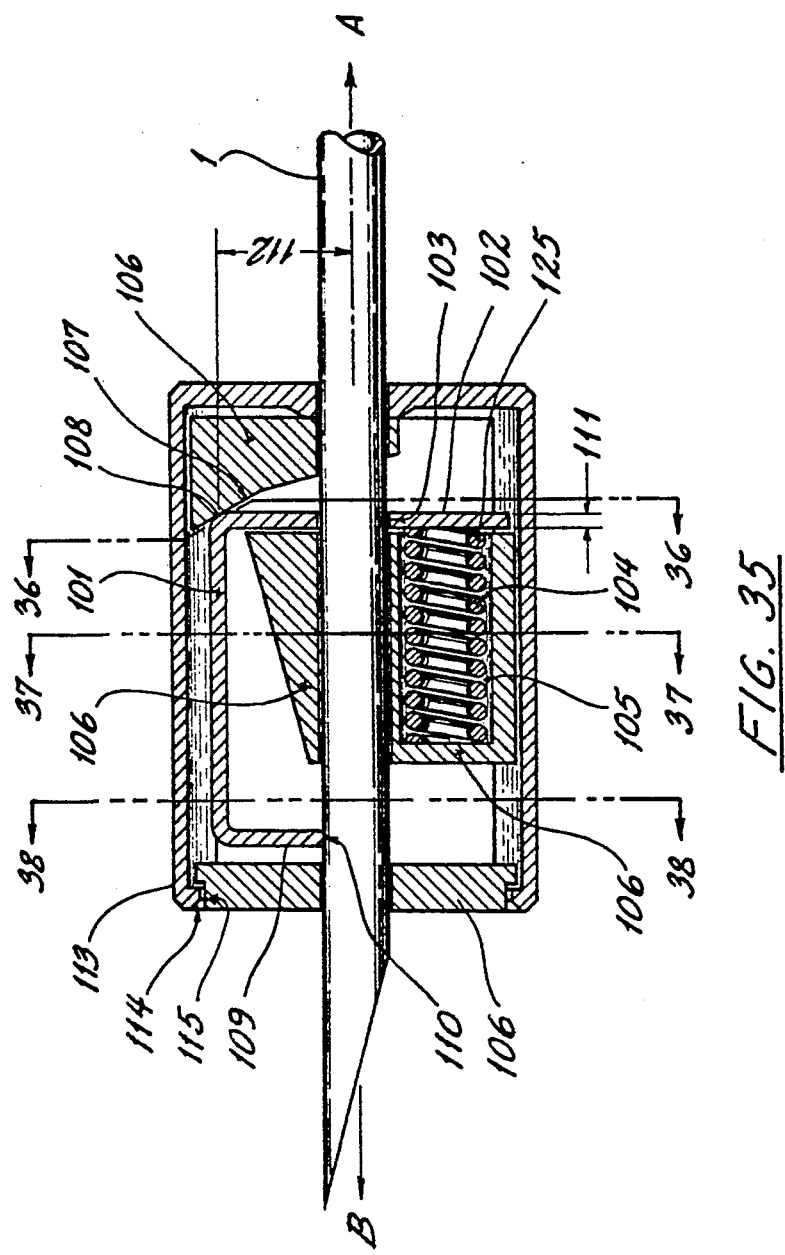
FIG. 36
FIG. 35

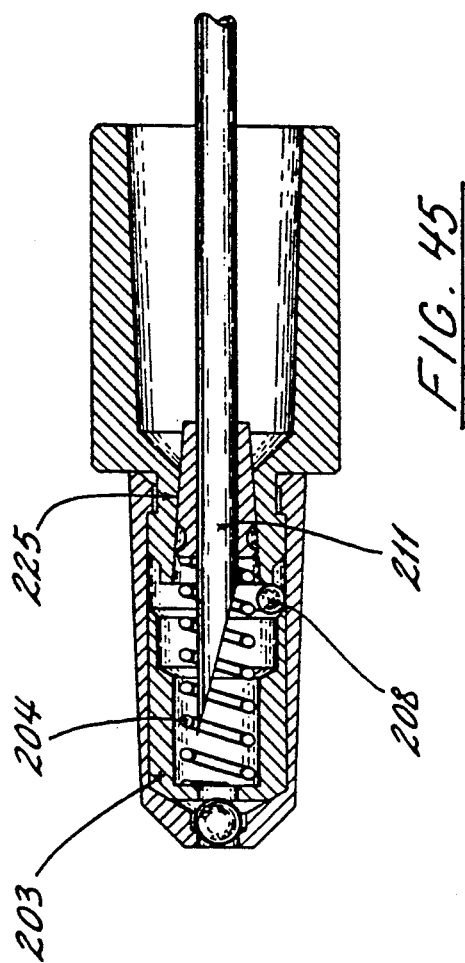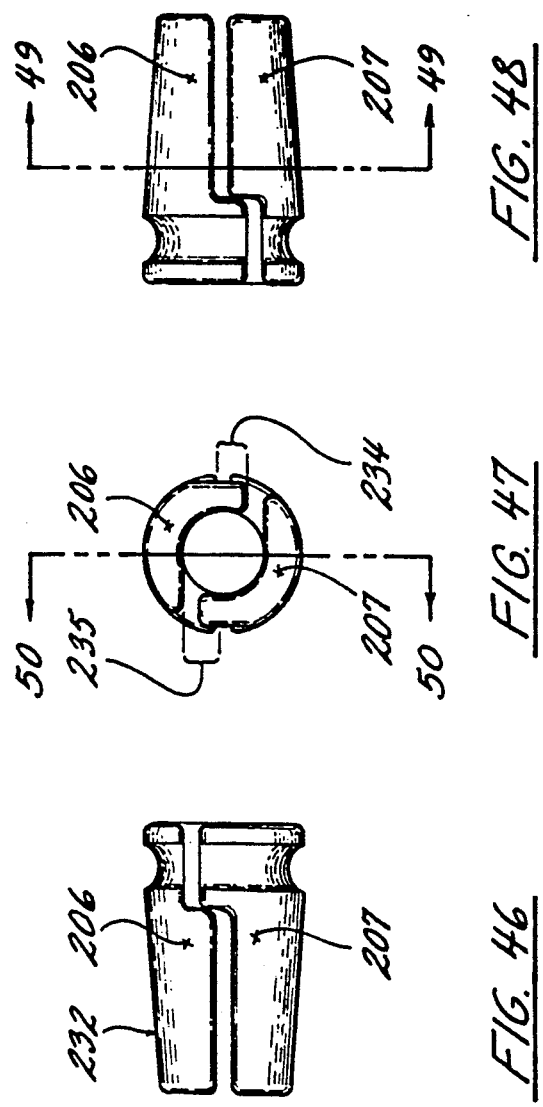

DISPOSABLE AUTOMATIC HYPODERMIC NEEDLE GUARD

This application is a continuation-in-part of Ser. No. 07/309,305 filed Feb. 1, 1989, abandoned. A related application is Ser. No. 07/672,651 filed Mar. 20, 1991.

1. FIELD OF THE INVENTION

This invention relates to the safe disposal of hypodermic needles by a guard device which protects the needle tip from exposure after use. More particularly, it relates to a tip protector which is storable on the needle and which automatically locks over the end of the needle when slid into position by the user.

2. BACKGROUND TO THE INVENTION 2.1 The dangers of infection from accidental contact with the pointed end of used hypodermic needles has long been recognized and is well documented. For example, refer to Jagger, Hunt, Brand-Elnaggar and Pearson, the New England Journal of Medicine, August, 1988. In most procedures, the greatest avoidable risk of accidental needle puncture, or "needle-stick", occurs during handling of the used needle, when it is generally inserted into a protective sheath for disposal. This action usually requires moving the hand which holds the sheath towards the pointed tip of the needle, and any inaccuracy in this operation raises the possibility of a puncture. The risk of this is greatly increased if the operator is working under stress, such as time-pressure or fatigue, or is handicapped by marginal eyesight or unsteady hands.

2.2 A number of devices have been developed to deal with the general problem of needle-sticks, and reference may be made to U.S. Pat. Nos. 4,747,835 (Sandhaus); 4,735,618 (Hagen); 4,735,617 (Nelson, Fieme); 4,731,059 (Wanderer, Sagsfretter); 4,725,267 (Vaillancourt); 4,720,285 (Pickhard); 4,623,336 (Pedicano, Kane); 4,430,082 (Schwabacher, et el), and 4,755,170 (Golden).

2.3 Some of these, for example Sandhaas, Neison/Flome, and Pedicano/Kane, provide an enlarged conical entry to the protective sheath, so that the resulting larger target reduces the chance of the operator missing the entry. This may be combined with some non-manual means of holding the sheath assembly, further reducing the risk. All of these devices require the operator to divert his attention from his immediate task and to exercise some measure of care in placing the needle into the sheathing device.

2.4 Others of these, for example Hagen and Vaillancourt, aspire to attain the desirable goal of keeping the hands wholly behind the sharpened tip of the needle during the manipulation of the protective device. The Hagen design stores the tip protector around the base of the needle, but in this mode the lateral retaining members are folded in an "arms akimbo" configuration, mending to either side of the needle in a manner which could interfere with the proper manipulation of the syringe and needle during insertion and removal. The Vaillancourt design mounts the tip protector at the distal end of a cylindrical bellows coaxial with the needle, which may be collapsed longitudinally to allow storage of the tip protector at the needle base. This is more compact, but requires care and attention during the needle sheathing action to ensure that the needle is properly located within the protector. Failure to do this could result in the needle becoming exposed again. Both designs appear to offer uncertainty of protection in the event of an impact against the tip of the needle, such as might occur if the latter were dropped. As both designs appear to employ flexed plastic or elastomeric joints or folds for their articulation, operation of the device might encounter significant stiffness, depending upon the desired mechanical strength of this articulation and the length of time over which the device was kept in the stored position prior to use.

2.5 Golden provides for a sealing cover to be placed over a needle tip after being slid down the needle from the base. This tip, made of absorbent material that is not normally stored on the needle prior to use, is not of a dimension that would fit conveniently within a storage cover. The positioning of this cover is either by means of eye judgment, relying on a marker on the needle; or by means of a thickened portion formed near the tip of a specially configured needle. This cover does not, however, fasten, clamp or lock onto the needle tip in any way. A needle-stick injury could simply occur by the accidental withdrawal of the cover from the tip.

2.6 Against this background, it is the object of this invention to provide a protective guard for hypodermic needles with the following useful functions:

2.6.1 It provides a protective guard which forms an integral part of the needle assembly and which is dimensionally shorter in length than the needle.

2.6.2 The protective guard may be stored prior to use at the base of the needle shaft in a manner which requires a minimum of space and is substantially unobtrusive.

2.6.3 The protective guard may be retained in its storage position by a retention means which allows the ready release of the protective device when it is to be moved into its protecting position.

2.6.4 The protective guard may be moved into its protecting position on the needle; tip following needle use in a way which requires no significant training, no manual skills, no visual acuity, or particular level of lighting.

2.6.5 The protective guard may be moved into its protecting position with the hands always behind the needle tip and with the motion of the hands always directed safely away from the needle tip.

2.6.6 The protective guard automatically detects the needle tip to establish its correct protecting position on the needle shaft with no judgement required of the operator.

2.6.7 The protective guard automatically locks itself to the needle shaft with no additional action required of the operator when it has reached the correct axial protecting position.

2.6.8 According to one further arrangement when the protective guard is locked in its protecting position the sharp tip of the needle is automatically covered by a substantial thickness of material to provide a high degree of protection against re-emergence of the needle tip from the protective cover.

2.6.9 When the protective guard is in its protecting position it presents a smooth, substantially unobtrusive surface with no protrusions.

2.6.10 When the protecting guard is in its protecting position the used needle may be handled and disposed of with no more than normal handling precautions than are customary for potentially contaminated medical materials.

2.6.11 When the protecting guard is used in association with an insertion needle within a catheter, the guard is automatically transferred from its storage position to the needle tip by the action of withdrawing the insertion needle from the catheter.

2.7 An important area of concern in the disposal of possibly contaminated needles relates to the use of intravenous catheters. In these devices, the needle is usually supplied in a pre-packaged assembly, already inserted inside a flexible, close-fitting catheter tube, the latter having a base with coupling means to allow the subsequent connection of tubing for intravenous infusion or similar procedures. The needle length is such that its point extends slightly beyond the distal end of the catheter, thus acting as a piercing means to allow insertion of the catheter and needle into a blood vessel in the patient. Thus such needles are known as "insertion needles".

2.8° Following insertion of the needle and catheter, the needle is withdrawn from inside the catheter and must be disposed of. At this point the operator's attention is taken up with other matters, mainly relating to the attachment of tubing to the catheter and controlling loss of blood, and this makes him significantly more vulnerable to needle stick accidents if he must divert his attention to safe disposal of the needle by conventional means.

2.9 By a simple adaptation, the subject protective guard may be attached to the catheter as part of the pre-packaged assembly, with the needle installed first through the guard and then inside the catheter. When the operator withdraws the needle from the catheter after insertion into the patient, the guard remains frictionally attached to the catheter, allowing the needle to slide freely through it in either direction, until the point of the needle is withdrawn inside the body of the guard. At this point the guard locks securely over the tip of the needle, allowing the operator to detach the guard from the catheter by a slight additional withdrawal force. The needle, with the guard in place, may be then disposed of without further attention from the operator.

2.10° In this way, no separate action or thought is required of the operator during the needle withdrawal process, since the guard is automatically applied as the needle point exits the catheter during the normal withdrawal sequence, and therefore no training is required in the use of the guard element.

2.11° These desirable qualities, as well as other features and characteristics are provided by the subject invention, using the arrangements, construction, components, and steps as described and illustrated hereafter in this disclosure, and which exemplify this invention.

3. SUMMARY OF THE INVENTION 3.1 According to this invention a secure means of automatically covering the pointed end or tip of a hypodermic needle is provided by a needle tip protecting device in the form of a protective guard which is initially stored on the barrel of the needle, remote from the tip, and which is displaceable to a position enclosing the needle tip where it automatically locks in this position serving as a protecting means for the needle tip. The protective guard may optionally be stored prior to use at the base of the needle. In this position it may further be contained within the usual protective sheath which covers a needle prior to use, and may thereby be supplied with the needle in its sealed and sterilized package.

3.2 By reason of the fact that the protective guard may be stored on the needle prior to the normal use of the needle, and occupies an insignificant, compact space, its presence produces a minimum interference with the normal use of the needle. In one application the protective guard may be stored adjacent to or even within the enlarged base of a catheter, in an unobtrusive manner that allows the catheter to be inserted in the normal manner.

3.3 After withdrawal of the needle following use, the tip of the needle can be immediately covered with the protective guard by a simple manual action of gripping the protective guard with the fingers, sliding it out of its storage position at the base of the needle, and continuing the sliding motion along the needle shaft until the guard just over-reaches the end of the needle. There it automatically locks in position with the tip of the needle safely covered inside the protective guard.

3.4 The protective guard achieves these effects by being provided with an internal energy storage element, such as a spring, that is capable of initiating a clamping force through a clamping mechanism. Generally, this clamping force is applied directly to the exterior surface of the needle shaft. A latching mechanism serves to suspend initiation of the clamping force prior to withdrawal of the needle tip within the protective guard. A trigger system releases the latching mechanism once the needle tip passes within the protective guard, thereby initiating the clamping force which is applied to the needle, and thereby locking the protective guard in place over the needle tip. These functions occur automatically and enclose the needle tip with a protecting means which is non-removeably engaged thereto.

3.5 The clamping force need only immobilize the protective guard against axial or longitudinal displacement on the needle. Further, its locking resistance need not be symmetrical. It is essential to have a high locking resistance against further removal of the guard from the needle. In the other direction resistance to the reemergence of the needle tip from the guard can be substituted or supplemented by arranging for an occluding element to occupy the path of the needle and serve as a containment means. Once the tip enters the guard the presence of such a blocking element ensures that the needle tip cannot re-emerge from the guard even where the locking resistance against displacement of the guard towards the needle base is overcome. When such a blocking element is present, it is sufficient for the clamping mechanism to provide only a uni-directional or one-way resistance to further removal of the guard from the needle. 3.6 A variety of modes for proving an engagement or locking means of locking the protective guard to the needle may be adopted. Some of these locking systems may be categorized as follows:

(1) a coaxial spring system wherein the spring grasps the needle shaft in a "constrictor" fashion;
(2) a "push nut" style mechanism wherein the edge at the end of a near-perpendicular leaf of metal is pressed into the side of the needle shaft;
(3) a tapered cavity or "chuck" system wherein a locking element is forced into locking engagement with the needle by jamming the locking element between the narrowing wall of the tapered cavity and the needle shaft; and
(4) a "canted plate" system whereby locking is effected by canting a plate having a hole therein through which the needle shaft passes in a close, sliding fit.

Other modes of engaging or fixing the needle with the guard may be provided as well, including the combination of the above modes with a occluding element, as mentioned in pard 3.5, above.

3.7 Several modes of providing a sensing and trigger means for detecting the presence of the needle tip within the protective guard, and thus activating the trigger-release function may be identified as follows:

(1) a transverse rotatable cylinder is biased to rotate but is restrained from doing so by the presence of the needle shaft passing transversely through the cylinder;

(2) a "lever arm" bears against the needle at one end and is biased to rotate and release the locking mechanism when the needle tip has been drawn past the bearing point; and (3) a "sensing ball" or "sensing pin" arrangement is provided whereby the withdrawal of the needle tip to within the protective guard allows a sensing element to move into the path vacated by the needle and release the locking system.

Other modes of providing a trigger-release system may be adopted as well.

3.8 The various modes of locking the protective guard to the needle may be combined with various latch and trigger mechanisms.

3.9 Optionally, the protective guard may be provided with an outer shell which free to rotate easily around its inner body, thus isolating the inner body from manually-applied torque which might tend to reduce its grip on the needle shaft after it locks in position on the needle tip.

3.10 The protective guard may be slid to the needle tip by the direct application of fingers to the guard. Alternately, handle means may be provided either in the form of an arm, or the like, attached to the guard body; or by use of a simple draw string that is initially stored on the protective guard by being wrapped around its exterior casing.

3.11 According to several embodiments of the invention, when the latch is released by the passage of the needle tip inside the end of the protective guard, a component of the trigger mechanism positions itself so as to close-off the needle opening in the end of the guard. This covers the needle tip with a substantial amount of material, providing a high degree of protection against impact on the end of the needle, such as might be caused by dropping the needle with attached syringe. It may also occlude the needle bore thereby reducing the tendency for fluids to drain therefrom.

3.12 The locking action of the protective guard on the needle shaft may be accomplished in one embodiment by using a simple coil locking spring coaxially surrounding the needle shaft in a constricting fashion. The spring may be made of any suitable material, but would typically be made of stainless steel. In its free state, the inner diameter of this spring is selected so that it tends to be slightly less than the outer diameter of the needle shaft. Prior to locking the protective guard on the end of the needle, the locking spring is maintained in a partially-unwound state by a spring retention means, such that the inner diameter of the spring is equal to or slightly greater than the outer diameter of the needle shaft, sufficiently to allow a close sliding fit and free relative rotational and axial motion of the protector over the needle. This partially unwound state is maintained by a torque applied at each end of the spring by two torque-sustaining members which are held rotationally coupled by a latch mechanism which serves as a release means when the needle tip enters the protective guard.

3.13 When this latch mechanism is released, the unwinding torque applied this spring is released as well, causing the spring to contract and clamp on to the needle. The release of the latch mechanism and corresponding release of the torque sustaining members and spring occurs automatically, when the tip of the needle is withdrawn inside one end of the protective guard by the operator sliding it past the tip of the needle.

3.14 The frictional grip between the locking spring and the needle shaft may optionally be augmented by a backup spring, concentrically surrounding the locking spring. This backup spring may be arranged to apply supplementary torque to the ends of the locking spring so as to wind it tighter, without significantly restraining rotational friction between the locking spring and the needle shaft.

3.15 As another alternate embodiment of the invention, the locking means comprises a leaf means which is preferably in the form of two or more hardened spring steel leaves, mounted on a surrounding narrow, circular rim concentric with the needle axis within a thrust-absorbing housing. Two leaves are provided for the convenience of the symmetry they provide, but an arrangement with a single leaf could also be adopted. In the case of dual or more leaves the radial leaves are formed so that they lie approximately in the form of a shallow cone angled so as to be pointed towards the needle tip and coaxial with the needle shaft, with the space between the inner ends of the leaves providing a close sliding fit with the outside of the needle shaft. This allows the latter to move, before the clamping effect is developed, freely between the leaves, in an axially direction.

3.16 This arrangement is recognizably similar to the familiar "push-nut" used to provide axial retention on unthreaded shafts and studs. In such a connector the outer ends of the leaves are joined in a shallow conic orientation by an exterior frame of material formed integrally with the leaves. The leaves may be of a size and position such that the potential spacing between the inner ends of the leaves, when nearly flattened, is significantly smaller than the diameter of the shaft. This dimensional feature would require that the inner ends of the leaves to be deflected outwards as the nut is pressed onto the shaft, thus deepening the initial conical form of the leaves. On applying reverse axial load on the portions of the leaves next to the shaft, directed towards the base of the conical form, the leaves tend to collapse inwards, cutting into the surface of the shaft, and firmly resisting relative axial .motion. The outward reaction force on the leaves is taken by the surrounding frame of spring material in tension.

3.17 In this embodiment of the present invention, the narrow rim joining the outer ends of the leaves is used solely to hold the leaves in their initial or unlocked position, and the diameter of the rim is such as to provide a slight interference fit in the inner bore of the body of the protective guard, thus retaining it frictionally in position in the bore.

3.18 Alternately, the radial reactionary compressive load on the locking leaves may be taken by the bore of the surrounding thrust-absorbing housing or body the locking device, against which the outer ends of the leaves press. The narrow rim joining the locking leaves, in such case, takes no significant fraction of this reaction force.

3.19 Locking of the guard to the needle shaft may be provided by applying an axial force to the inner ends of the leaves through a pressure sleeve which is biased to move axially along the needle shaft under spring pressure, in a direction which tends to collapse the leaves radially inwardly, forcing them to come in tight frictional contact with the needle shaft.

3.20 If the needle shaft then attempts to move axially in the same direction as the pressure sleeve, the leaves will tend to collapse further inwards against the needle shaft, because of friction between the two. Provided the tangent of the complement of the angle between the locking leaves and the needle axis, as measured in the axial plane, is equal to or less than the coefficient of friction between the end of the leaves and the surface of the needle shaft, slippage between the leaves and needle shaft will not occur. Increasing the axial load will cause a corresponding increase in the frictional grip between the two until a point is reached where mechanical deformation alters the geometry or material failure occurs.

3.21 According to this alternate embodiment of the invention, in the unlocked state, the pressure sleeve is held away from the locking leaves by a transverse latch shaft, through which the needle shaft passes, preventing its rotation. On the exiting of the end of the needle from the latch shaft, the latter rotates, releasing the pressure sleeve and allowing it to move axially and lock the leaves against the needle shaft. The now-rotated transverse latch shaft serves to block passage of the needle tip through the tip protector, preventing the tip protector from sliding back down the needle towards the needle base.

3.22 In yet another third embodiment of the invention, the locking leaves as described above are replaced by a plurality of locking elements or jaws of hardened material, radially disposed about the needle shaft, and contained within a gradually tapered or narrowing cavity within the body of the guard device which constitutes a conic chuck means. Such jaws may be in the form of bisected conical segments with their bisecting edges presented towards the needle.

3.23 In the unlocked state, these jaws may be maintained loosely in the bore but in a generally uniform distribution about the needle axis by compliant fingers engaging each-jaw. These fingers may optionally be constituted by axial extensions of the pressure sleeve as described above.

3.24 From its unlocked state, the pressure sleeve may be released by a trigger mechanism and urged by an energy storage element, such as a compressed spring, to move axially, forcing the jaws into the conic chuck means and thereby producing a high radial gripping force between the jaws and the needle shaft because of the gradual narrowing taper of the cavity walls and the consequent high mechanical force advantage that this creates.

3.25 This arrangement is closely analogous to the familiar three-jawed drill chuck, where the axial force required to produce the required clamping force is usually developed by some form of screw thread. In this embodiment, the taper of the containment cavity is much more gradual, chosen consistent with the various parts to produce a self-locking action which increases as axial force is applied to the needle shaft in the same direction as the force of the pressure sleeve. It follows that motion of the needle shaft in the opposite direction will produce lessening of the grip of the locking jaws, but this may be resisted by selecting a spring for the pressure plate that is of sufficient strength to resist loosening of the clamping action 3.26 In yet another fourth embodiment of the invention, the locking jaws as described above may be replaced by rolling elements in the form of a plurality of substantially cylindrical rollers of hardened material, uniformly disposed about the axis of the needle shaft, with the axis of each roller in a plane perpendicular to the needle shaft axis, and with each roller making tangential, or crossed-cylinder contact with the surface of the needle shaft. The rollers are again contained in a gradually tapered cavity within the body of the guard device, each side of this cavity in this case being a plane surface forming part of a side surface of a conical polyhedron coaxial with the needle shaft.

3.27* In the unlocked state, these rollers are retained loosely in the bore by a surrounding containment cage, optionally constituted by an axial extension of the pressure sleeve as described above.

3.28* From its unlocked state, the pressure sleeve may be released to move axially, bringing the rollers into contact between the wall of the tapered cavity on the outside and the needle shaft on the inside. Subsequent axial motion of the needle shaft in this same direction of motion causes the rollers to roll axially with the needle towards the smaller end of the tapered cavity, increasing the force of contact between the tapered cavity wall and the needle shaft. This results in high frictional grip between the rollers and their containment cavity on the outside, and the needle shaft on the inside, sufficient to block further motion of the needle in this direction. Once jammed in this locking position continuing pressure from the pressure sleeve will tend to keep the protective guard in this locked condition.

3.29* In yet another fifth embodiment of the invention, the rollers described above are replaced by a plurality of hardened spherical balls, uniformly disposed about the needle shaft axis, with the centers of the balls in a common plane perpendicular to the needle shaft axis, and with each ball making contact with the surface of the needle shaft. These balls may be contained within a gradually tapered conical bore or cavity within the body of the guard device, loosely confined within a containing cage which may be an axial extension of the pressure sleeve as described above.

3.30* In yet another sixth embodiment of the invention, the various locking mechanisms described above are replaced by a combined latching and locking plate, referred to below as the lever arm. This lever arm may be formed of a flat, hardened strip, bent in the shape of a broad U with two legs of unequal proportions, lying in the plane of the needle shaft. The locking plate portion of this lever arm, which is the longer of the two unequal legs of the U, is provided with a hole through its approximate center which will allow a near close-fitting but free passage of the needle shaft through this leg, with the end of the shorter leg of the U in contact with that portion of the needle shaft extending towards its pointed end. Conveniently the hole through the locking plate is oriented to allow free passage of the needle shaft when the locking plate is perpendicular thereto. A precise perpendicular orient action is not, however, essential, so long as the locking plate may be canted between the free passage position and a locking position.

3.31 The lever arm, which serves as an alignment means for the locking plate, is contained within the body of the guard device, with the bend of the longer leg of the U held in axial contact with an internal face of the body, by the force of a helical compression spring. The point of contact between the lever arm and the internal face serves as a pivot point and clearance is provided for the lever arm to pivot about this point. The spring is contained within a cylindrical cavity in the body on the opposite side of the needle shaft from the pivot point, the axis of the cavity being close to and parallel with the needle axis, with the free end of the spring extending from the cavity to press axially against the outer end of the longer leg of the lever. This biases the longer leg or locking plate portion of the lever arm to become canted with respect to the needle shaft. With the needle extending through the body of the guard device, the lever arm is constrained by the contact of its shorter leg with the side of the needle shaft closer to the tip end to remain with its longer leg held at an angle, vis perpendicularly to the needle axis in the preferred embodiment, that allows free passage of the needle. Optionally, this shorter leg may be omitted, with the lever arm contacting the needle directly.

3.32 When the guard is slid along the needle so that the end of the latter has entered the guard body and moved past the point of contact with the end of the shorter leg of the lever arm, the lever arm is freed to turn about its pivot point under spring pressure so that the hole in the locking plate is no longer coaxial with the needle. This causes substantial frictional contact and locking engagement with the needle shaft.

3.33 With the selection of the known appropriate geometry of the lever and needle shaft, critically related to the coefficient of friction between them, the frictional grip between the lever and the needle shaft may be arranged to always be greater than the applied axial force on the needle. The lever can thus become self-locking on the needle shaft, without regard to the spring pressure. Thus further motion of the needle is prevented until material failure occurs. However, pressure from the spring serves as a canting means and is preferable as a secure means for ensuring that the locking condition is maintained.

3.34 By way of further security, the shorter leg of the lever arm which becomes displaced into the needle path once the needle is no longer in contact with this leg, serves to block the reverse displacement of the needle, this further containing the needle tip within the protective guard.

3.35 This arrangement is recognizably similar to certain makes of automobile jacks, in which the weight of the vehicle is carried upon a forged steel bracket sliding on a vertical cylindrical steel support column. Frictional grip between the bracket and column is established by one or more rectangular steel plates fitting closely but freely about the column, bearing axially on their one end against a shoulder in the bracket, and being directed away from perpendicularity with the column axis by a compression spring. The arrangement permits the bracket to move in an upward but not downward direction on the column, in the manner of a ratchet. Lifting action is applied by a hand lever pivoted within the bracket, which transmits force to the column through a second close-fitting plate or plates, bearing on their one end against a shoulder on the lever, in a manner allowing the lever and associated friction plates to press downwards against the column when the lever is operated, thus forcing the bracket upwards on the column and raising the vehicle. Lowering the jack is accomplished by detaching the lever handle and using it to slightly move the tint-mentioned plate or plates towards a position more nearly perpendicular to the axis of the column, thus releasing the frictional grip of the bracket with the column.

3.36 Motion of the needle in the opposite direction in one configuration of this design releases the self-locking action, but re-emergence of the needle point from the guard is blocked by the presence of the shorter leg of the lever across the path of the needle. An alternate configuration may be provided which effects locking against motion in both directions.

3.37 A loosely-fitting cylindrical sleeve surrounding the body of the guard is preferably added to provide rotational isolation from the means used to move the guard axially on the needle shaft, thereby preventing the forcible removal of the protective guard by accidental or deliberate twisting of the guard relative to the needle. Such a sleeve may optionally be applied to all embodiments of the protective guard.

3.38 Thus, to summarize for this last embodiment, the locking effect is achieved by canting a locking plate having a hole therein through which the needle slides with a near close, but loose, sliding fit. A locked condition is effected automatically by means of a spring and lever arm to cant the locking plate. No canting force is applied to the locking plate until the needle tip is withdrawn into the protective guard. At that point the lever arm rotates under the influence of the spring, applying a canting force to the locking plate and thereby locking the protective guard to the needle.

3.39 In a further embodiment of the invention a sensing ball mechanism is employed in order to effect engagement of the protective guard to the needle. A locking assembly of the "chuck" type is provided within a main body that envelopes the needle by a transverse passage and is slidable thereon. This body is provided with a tapered or narrowing interior cavity which lies adjacent to the needle bore, and conveniently may surround the needle shaft. A locking element conveniently, for the benefit purposes of symmetry, in the form of a pair of conically shaped locking jaws (although a single jaw element could be adopted) is present within the cavity, these locking jaws being displaceable between the broader and narrower regions within the interior cavity. A spring means is provided within the main body which biases the locking jaws towards the narrowing regions of the cavity whereby the locking jaws may be forced into jamming engagement between the needle bore and cavity wall, locking the protective guard to the needle.

3.40 A latch or latching means releaseably retains the locking element from advancement into the tapered cavity. A trigger means, based on a sensing element, operates to release the latching means when the tip of the needle is withdrawn into the protective guard, allowing the spring means to force the locking jaws into locking engagement with the needle.

3.41 In this embodiment this latching or retention means is of the ball-in-socket type wherein a latching ball lies partially within a groove or socket generally, or against a stopping surface, formed within the side of the locking jaws. This latching ball also partially rests against a stop surface formed on the interior of the main body of the guard. It is therefore inter-engaged with both elements. The pair of conical jaws are loosely inter-fitted with portions of each over lapping or inter-leaved with the other. This permits a single latching ball to be used to retain both of the jaws in their latched position.

3.42 The latching ball is held within the groove in the jaws by a further ball retention element, which may be in the form of a cylindrical sleeve or plunger which is able to slide from a position where it contains the latching ball within the groove on the jaws, to a position where it no longer contains the ball whereupon the ball may withdraw from the groove and release the locking jaws. This cylindrical sleeve retention element, therefore, serves as a release means for the jaws, thus forming part of the latching means.

3.43 A trigger means serves to hold the ball retention element in its ball-retaining position while the needle shaft passes entirely through the needle guard. Upon activation, this trigger means allows the retention element to be displaced to a ball-releasing position, once the needle tip is withdrawn within the protective guard.

3.44 This trigger means is of the sensing ball type wherein a steel ball serves as the sensing means for reacting to the presence or absence of the needle shaft within the guard. This sensing ball partially rests between a stop surface on the ball retention element and a further stop surface on the interior of the guard body. By reason of its contact with the stop surface on the ball retention element, this second ball prevents the ball retention element from moving and thereby releasing the first ball and latching system.

3.45 This sensing ball is, however, also retained in place by the needle shaft against which it rests, and towards which it is biased to move by pressure from the ball retention means. This pressure arises from a spring means which, conveniently may be the same spring means that applies pressure against the locking element. This second sensing ball is directed by the inclination of the further stop surface on the guard body to be displaced into the path of the needle. It is blocked from so moving by the needle, so long as the needle passes fully through the guard.

3.46 Once the tip of the needle is withdrawn into the guard past the sensing ball, leaving this second or sensing ball no longer in contact with the needle the sensing ball will move into the path previously occupied by the needle. This displacement of the sensing ball then allows the ball retention element to move sufficiently to release the latching ball, and thereby release the jaws in order to effect locking of the guard to the needle.

3.47 Thus, in this embodiment the latching means is distinctly removed from the trigger means, and two independent parts, the latching ball and the sensing ball must both be displaced from their positions in order for locking to occur.

3.48 The locking force of the jaws within the chuck is enhanced by any attempt to further remove the guard from the needle. Conversely, it is reduced by an attempt to cause the needle tip to re-emerge from the guard. Conveniently, the presence of the sensing ball in the needle path can serve to prevent such a reemergence.

3.49 Thus, we summarize this last embodiment as providing a tip protective guard for covering the tip of a needle of comprising:

(1) a main guard body provided with a passage therethrough capable of enveloping a needle inserted therein, said body having a narrowing interior cavity;

(2) a locking element slideable within said cavity capable of grasping and locking relative movement between said needle and said body in at least one axial direction of said needle;

(3) spring means capable of biasing said locking element to advance into the narrowing interior of said tapered cavity and lockingly engage said needle in at least one axial direction of said needle;

(4) latching means positioned to releaseably restrain said locking element from being advanced into said cavity;

(5) trigger means, positioned to release said latching means when the tip of said needle is-withdrawn into said guard body; and (6) containment means for preventing re-emergence of said needle tip from said body once the needle tip has been withdrawn into said body.

3.50 Further, in such needle tip protector said latching means more particularly comprises a latching ball positioned between a shoulder on said locking element and a shoulder on the guard body, said latching ball being releaseably retained in a latching position against said shoulders by a coaxially displaceable retention means positioned to release said latching ball upon displacement of said retention means, and wherein said trigger means comprises a second ball constituting a sensing ball, positioned so as to restrain said sleeve from displacement, said sensing ball being restrained in a latching position by the presence of the aforesaid needle within the guard body and being positioned such that withdrawal of the end of said needle to within the guard body allows release of said sensing ball by permitting said sensing ball to move into the path previously occupied by the needle.

3.51 The foregoing constitutes a description of four exemplary modes by which the protective guard may be clamped or locked in place so as to conceal a needle tip. Three mechanisms for acting as a latching and trigger means has been described, namely a transverse locking shaft or cylinder, the lever arm and the sensing and latching ball systems. Details of exemplary latching and trigger mechanisms that may be employed are further described in the following sections in conjunction with the description of the preferred embodiments.

3.52 These and further features of the invention and its various aspects will be better understood from the description of preferred embodiments which now follow.

4. DESCRIPTION OF PREFERRED EMBODIMENTS

4.1 SUMMARY OF THE DRAWINGS

FIG. 4 shows one embodiment of the guard device employing a rotational locking spring latch, with the device in the unlocked state prior to disposal.

FIG. 5 is a simplified end view of FIG. 4 showing the principal latching components, in the unlocked state.

FIG. 6 is a top view of FIG. 5.

FIG. 10 shows a second embodiment of the locking spring guard device employing a transverse plunger latch, with the device in the unlocked state prior to disposal.

FIG. 11 is a cross-sectional end view of FIG. 10, showing the principal latching components in the unlocked state.

FIG. 18 is a partial cross-section of the device in the alternate embodiment employing locking leaves, shown in its unlocked state.

FIG. 19 is a partial cross-section of FIG. 18 showing the latch shaft in its unlocked position.

FIG. 20 is a cross-section of the device of FIG. 18 in its unlocked state, rotated ninety degrees from FIG. 18.

FIG. 21 is a cross-section of FIG. 20 showing the locking leaves in their unlocked position, viewed from within.

FIG. 29 is a partial cross section of the device in the embodiment incorporating locking rollers within a tapered cavity, shown in its locked state.

FIG. 30 is a cross sectional end view of FIG. 29.

FIG. 31 is a partial perspective view of the locking sleeve portion of FIG. 29, showing the placement of the locking rollers within their containment means.

FIG. 32 is a partial cross-section of the device in the embodiment incorporating locking balls within a conical bore, shown in its locked state.

FIG. 33 is a cross-sectional end view of FIG. 32.

FIG. 34 is a partial perspective view of the locking sleeve portion of FIG. 32, showing the placement of the locking balls within their containment means.

FIG. 35 is a longitudinal cross-section of a canted-plate locking device showing the relationship of the parts in the unlocked state.

FIG. 36 is a cross-sectional view showing the locking lever contained within its cavity in the body of the device.

FIG. 45 shows the device of FIG. 39 with the needle grasped by the guard element.

FIG. 46 is a side view of the jaw element of FIG. 39.

FIG. 47 is an end view of the jaw element of FIG. 39.

FIG. 48 is a further side view of the jaw element of FIG. 39.

Figure 1:
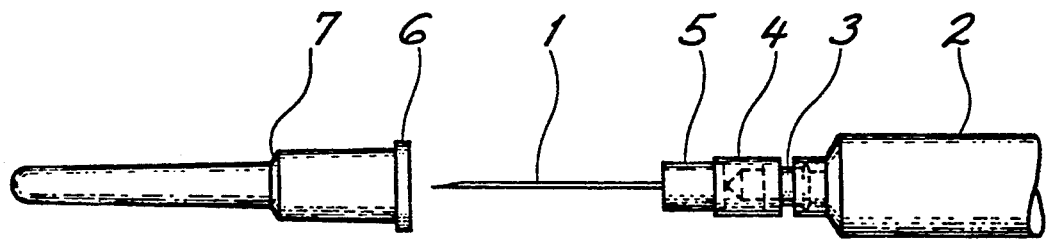
FIG. 1 shows a hypodermic needle fitted with the subject guard device, mounted on a syringe, and with the needle removed from its protective sheath preparatory to use.

4.2 DETAILED DESCRIPTION OF EMBODIMENTS 4.2.1 Referring to FIG. 1, the hypodermic needle 1 is attached to the syringe 2 by a needle connector or base element 3 of conventional design as regards its attachment to the syringe. The needle is optionally provided with a guard retainer 4 in the form of a hollow cylinder coaxial with the needle, with one end attached to the needle connector element 3, and with its other end directed towards the opposite or tip-end of the needle. This cylinder 4 attaches frictionally to the outer circumference of the guard device 5, hereinafter referred to as the "guard" or "protective guard". The guard may be removed axially from the guard housing 4 with normal finger effort, and thereafter may be slid axially with slight or no frictional resistance along the length of the needle. Alternately, the retainer 4 may be detached from the base 3 and used as a gripping means to slide the guard along the needle. While the retainer 4 provides convenience in coupling and handling the parts of the needle assembly, it is purely optional. If omitted, the guard 5 may be provided with a tight sliding fit on the needle 1 that will allow it to be stored on the needle 1 near the base 3.

4.2.2 Prior to use, the needle 1, guard retainer 4, and guard 5 may be stored in a protective sheath 6 of conventional design. The sheath 6 may be frictionally retained axially on the retainer 4 by inwardly-directed detent projections on the inner bore of the sheath entry opening, following well-established practice. Such established practice allows the needle to be retained within and gripped by the protective sheath while fitting the needle to the syringe or other device. The frictional coupling between the sheath 6 and retainer 4 is selected to release more easily than the coupling between the retainer 4 and needle base 3. This allows for removal of the sheath 6 without disturbing the retainer 4 or guard 5. The sheath 6 may optionally be provided with an inner shoulder 7 which will axially bias the guard 5 towards its stored position inside the retainer 4.

Figure 2:
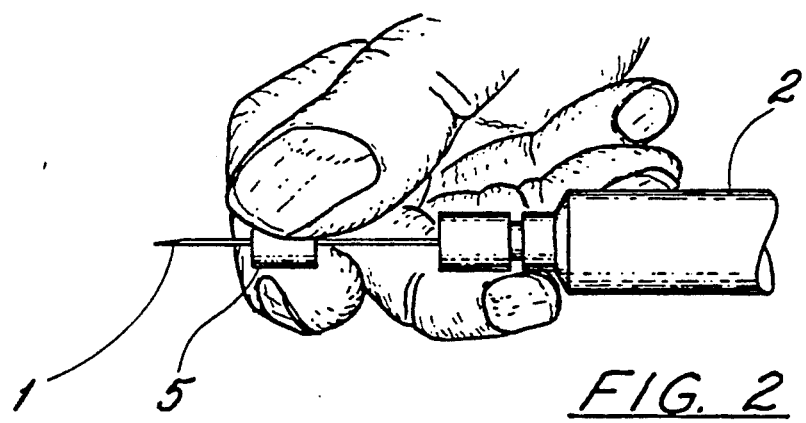
FIG. 2 shows the needle following use, with the subject guard device being slid towards the end of the needle by hand as the first step in the disposal sequence.

4.2.3 Referring to FIG. 2, all motions of the guard 5 during the disposal process are axial and directed away from the point of the needle 1, with the hands held away safely to the rear of the latter. Provided the guard 5 is not slid beyond the point of the needle 1, it may be slid in either direction along the needle, and may be returned to its stored position in the retainer 4 if desired. While frictionally stored in and when released from its retainer 4 the guard 5 is in its unlocked state.

Figure 3:
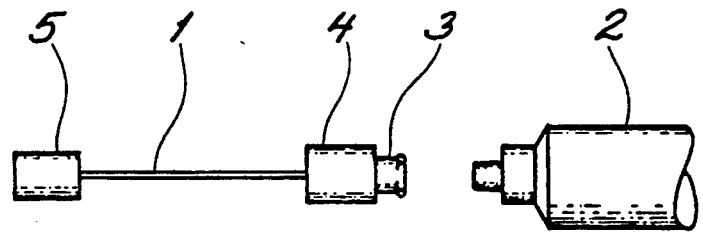
FIG. 3 shows the guard device locked automatically over the end of the needle, and the needle removed from the syringe for disposal.

4.2.4 As shown in FIG. 3, when the guard 5 reaches the end of the needle 1 and when the point of the needle is entirely enclosed within the guard, an armed locking mechanism within guard 5 is released to firmly grip the guard to the needle 1. One advantage of the exemplary trigger mechanism described next is that the opening in the outer end of the guard is closed-off to completely cover the point of the needle against accidental protrusion, even in the event of failure of the locking mechanism to hold the guard in place against impact, such as may be caused by dropping the needle and attached syringe. The guard 5 is now in what is referred to herein as its locked state.

4.2.5 Referring to FIG. 4, the body of the guard in this first embodiment is composed of three principal cylindrical parts; inner core 8, outer core 9, and shell 10. With other components omitted, the inner and outer cores are free to rotate with respect to one another about their common longitudinal axis.

4.2.6 At the larger open end of the outer core 9, where it forms a meeting face 11 with the inner core 8, radial support of the two mating parts with respect one another is provided by the common diameter 12. Similarly, at the opposite end of the assembly, relative radial support is provided by common diameter 13.

4.2.7 Axial positioning of the inner core 8 and the outer core 9 is maintained in the one direction by mating face 11, and in the opposite direction by the shell 10, which is fitted with inwardly directed flanges 14 at each end, each of which bears against the axial face of a circular coaxial rabbet 15 in the end face of inner core 8 and outer core 9.

4.2.8 The shell 10 is so dimensioned as to allow it to be pressed over the inner and outer cores during assembly, and to snap into position as shown, forming a loose fit with the inner and outer core to allow free rotation of all three components relative to one another.

4.2.9 The inner core 8 and the outer core 9 each have a central axial bore 90,91 respectively, sized to allow free passage of the shaft of the needle 1 with a close sliding fit. Surrounding the needle shaft 1 is a close-wound locking spring 16, whose unrestrained or free inner diameter is significantly less than the outer diameter of the needle 1. The locking spring 16 is accommodated within the inner core 8 by axial bore 17 and within the outer core 9 by axial bore 18.

4.2.10 Each end of the spring 16 is turned outwards at ninety degrees to form a radial extension 19 and 20. Extension 19 fits into an axial groove 21 in inner core 8 extending the full length of bore 17, and extension 20 fits into axial groove 22 in outer core 9 extending the full length of bore 18. By this arrangement, the inner core 8 and the outer core 9 may be rotated with respect to one another to apply torque to the spring 16 about its longitudinal axis. Such torque may be applied with two tools such as spanner wrenches, fitted to the outer face of the inner core 8 at spanner holes 23, and to the outer face of the outer core 9 at spanner holes 24.

4.2.11 In the embodiment shown in this disclosure, the locking spring 16 is wound with a right-hand spiral, similar to a right hand screw thread. Turning each spanner wrench in a clockwise direction with respect to the other, as viewed from the outside end of the guard 5, will cause torque to be applied to the spring 16 in such a direction as to cause it to unwind and thereby increase its diameter. The extent of this increase in diameter is limited by the diameter of bore 17 in the inner core 8 and by bore 18 in the outer core 9. Bores 17 and 18 are of equal diameter, thus forming a substantially continuous cylindrical surface coaxial with the needle shaft 1.

4.2.12 Bores 17 and 18 are of such a diameter that wren the spring 16 has been rotationally expanded to completely fill these bores, the inner diameter of the spring 16 has increased to be sufficiently larger than the outer diameter of the needle shift 1, to allow the needle 1 to move freely both axially and rotationally through the center of the guard 5. On releasing the torque applied with the spanner wrenches, the locking spring 16 rewinds itself tightly around the needle shaft, producing a substantial frictional grip between the spring 16 and the needle I in an axial direction.

4.2.13 The rewinding effort of the locking spring 16 may be augmented by backup spring 2.5, which is loosely accommodated in the annular space 26 between bores 12 and 13. One end of spring 25 is turned outwards at ninety degrees to form a radial extension 27, which fits into longitudinal groove 28 extending part way along the outer wall of bore diameter 12. The opposite end of spring 25 is turned inwards at ninety degrees to form radial extension 29, directed inwards to fit into groove 30 extending partway along the length of journal diameter 13.

4.2.14 During assembly of the guard 5, the inner core 8 and the outer core 9 are separated axially by an amount sufficient to disengage extension 20 of locking spring 16 from groove 22 of the outer core 9, while retaining engagement of extension 19 in groove 21 of inner core 8. Because of the greater length of groove 28, extension 27 of backup spring 25 remains engaged with the outer core 9, and extension 29 remains engaged with groove 30 of the inner core 8. This allows clockwise torque to be applied to the backup spring 25 using the spanner wrenches, without applying torque to locking spring 16. When grooves 21 and 22 are in alignment, and while this torque is maintained, the inner core 8 and the outer core 9 are moved together axially, reengaging extension 20 of locking spring 16 in groove 22. On releasing the applied wrench torque, the torque applied to the backup spring 25 is transmitted to locking spring 16, increasing its tightness of wrap around the shaft of the needle 1, and greatly adding to the frictional grip between locking spring and needle shaft.

4.2.15 With the shell 10 in place as shown in FIG. 4, no significant torque can be applied to either the inner core 8 or the outer core 9 by normal handling of the outer surface of the sleeve 10. This prevents the grip of the locking spring 16 from being degraded by applying an inadvertent clockwise torque to either the inner or outer core. Such a torque, if applied, would tend to unwind the locking spring and reduces its frictional grip.

4.2.16 The outer surface of shell 10 may be provided with a number of ribs, rings, grooves, knurls, or similar provisions to increase the grip in the axial direction between the operator's fingers; or, provide attachment means for a separate manipulative implement to be connected to the surface of shell 10, as further described below.

4.2.17 To allow axial motion of the guard 5 along the needle 1, it is necessary to hold the locking spring 16 in its expanded or partially unwound state, as described above. This requires holding the inner core 8 and the outer core 9 in their rotational relationship after clockwise torque has been applied to one with respect to the other.

4.2.18 In the embodiment shown in FIG. 4, this holding action is provided by a cylindrical member in the form of rotational latch 31, placed transversely in the body of the inner core 8 with its axis close to and parallel with the meeting plane 11, which forms the end face of the outer core 9.

4.2.19 The body of latch 31 is substantially cylindrical in form, with a semi-cylindrical extension 32 protruding beyond the diameter 12 of the inner core 8. This extension 32 forms a plane surface 32a lying along the plane of the axis of latch 31, and is shown more clearly in simplified end view FIG. 5 and simplified top view FIG. 6. This plane surface 32a extends into a notch 33 in the end face of outer core 9. One side of this notch 33 is in a plane radial to the cylindrical axis of the inner core 9, parallel to plane surface 32a of latch 31; and the other side is in the form of a spiral ramp, shaped to provide clearance with the cylindrical surface of the protrusion of latch 31.

4.2.20 The point of closest engagement of latch 31 with notch 3, shown as 34, lies on the diametral plane of latch 31, but at a distance 35 from its axis. The direction of the combined torques of the locking spring 10 and the backup spring 25 presses the plane face of notch 33 against the plane face 32a of latch 31, and this tends to rotate latch 31 in a clockwise direction as viewed in FIG. 4.

4.2.21 The needle shaft 1 passes through a hole 36 in latch 31 which is transverse to the rotational axis of the latch, thus preventing its rotation about this axis. The engagement of latch 31 with the notch 33 in the end face of outer core 9 prevents the rotation of the outer core 9 with respect to the inner core 8. This is because the latch 31 is transversely placed in the body of inner core 8, and is prevented by the presence of needle 1 from rotating about its own axis and out of engagement with notch 33.

Figure 7:
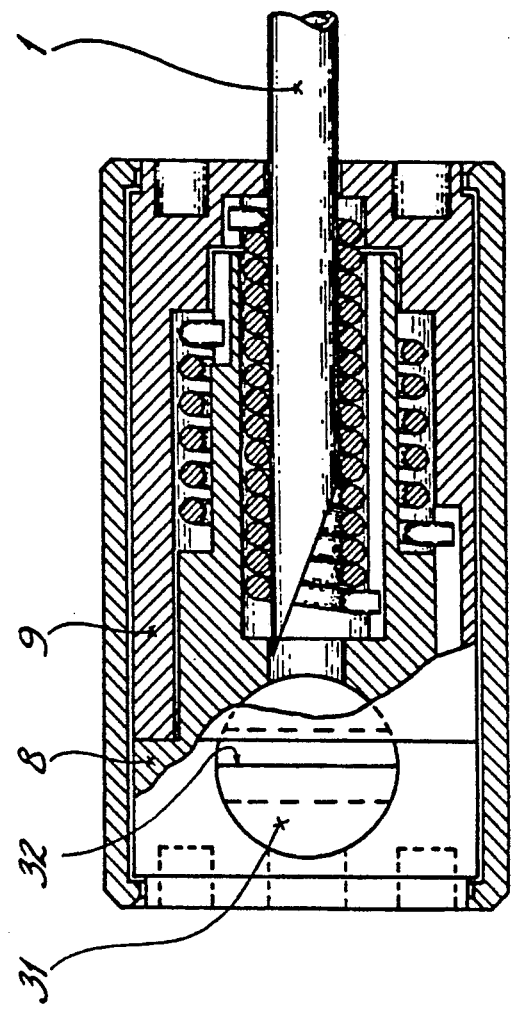
FIG. 7 shows the device of FIG. 4 with the end of the needle drawn inside the device, past the latch, and with the device locked onto the needle.

4.2.22 If the needle shaft 1 is withdrawn through the body of guard 5 and the tip of the needle disengages the latch 31 as shown in FIG. 7, then the latch rotates as a result of the torque applied to the plane face 32a. This disengages the latch from notch 33, and allows the rotation of the outer core 9 under the combined torque of the locking spring 16 and backup spring 25. This action is shown in simplified form in end view FIG. 8 and top view FIG. 9.

Figure 8:
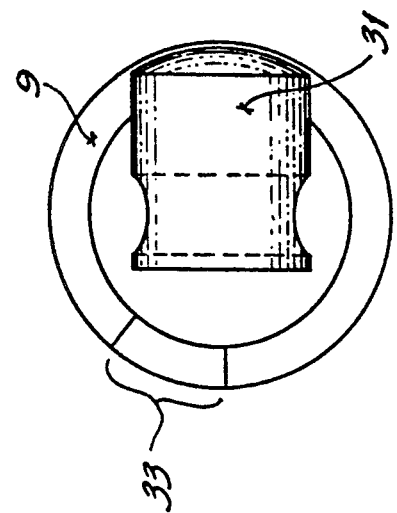
FIG. 8 is a simplified end view of FIG. 7, showing the principal latching components, in the locked state.

4.2.23 The dimensions of the locking spring 16 are chosen with respect to the outside diameter of needle shaft 1 so that the outer core 9 rotates approximately one-half turn about its axis, as locking spring 16 rewinds from its expanded diameter within bore 12 to its fully-locked state, wrapped tightly about the needle shaft 1. This is shown in FIG. 8, where notch 33 is diametrically opposite to its position shown in FIG. 5.

Figure 9:
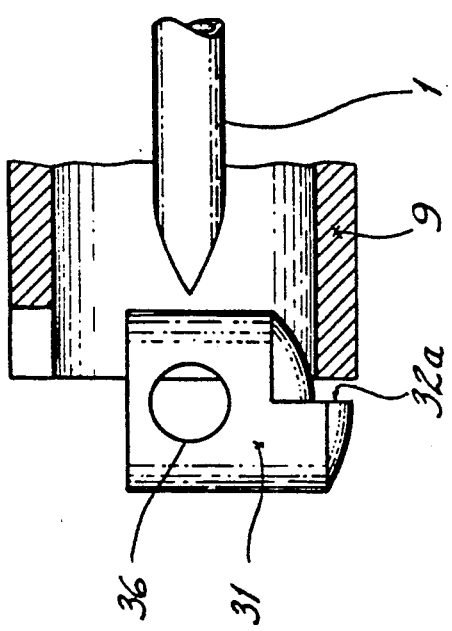
FIG. 9 is a top view of FIG. 8.

4.2.24 With the latch 31 rotated to the position shown in FIG. 7 and FIG. 9, the tip of needle 1 is prevented from re-emerging from the guard 5 in the event of failure of the locking spring 16 to withstand an externally applied force against guard 5 directed towards the base of the needle 1.

4.2.25 FIG. 10 shows a second embodiment of this first device, in which the rotational latch 31 of FIG. 4 is replaced by a cylindrical plunger latch 36, placed transversely in the body of inner core 8 which serves as a "sensing pin". As shown in cross section FIG. 11, the outer end 36a of the latch 36 is of approximately spherical form, and is in contact with the cam surface 37 formed as an outward extension of bore 12 of the outer core 9. The remaining components of the embodiment are substantially the same as described for FIG. 4.

4.2.26 The combined torques of locking spring 16 and backup spring 25 tend to rotate outer core 9 in a clockwise direction with respect to the inner core 8, as viewed in FIG. 11. This develops a force against the spherical outer end of plunger 36 with a component axial to plunger 36 tending to move the plunger inwards. Inwards motion of plunger 36 is blocked by the presence of needle shaft 1, thus preventing rotation of outer core 9 relative to inner core 8.

Figure 12:
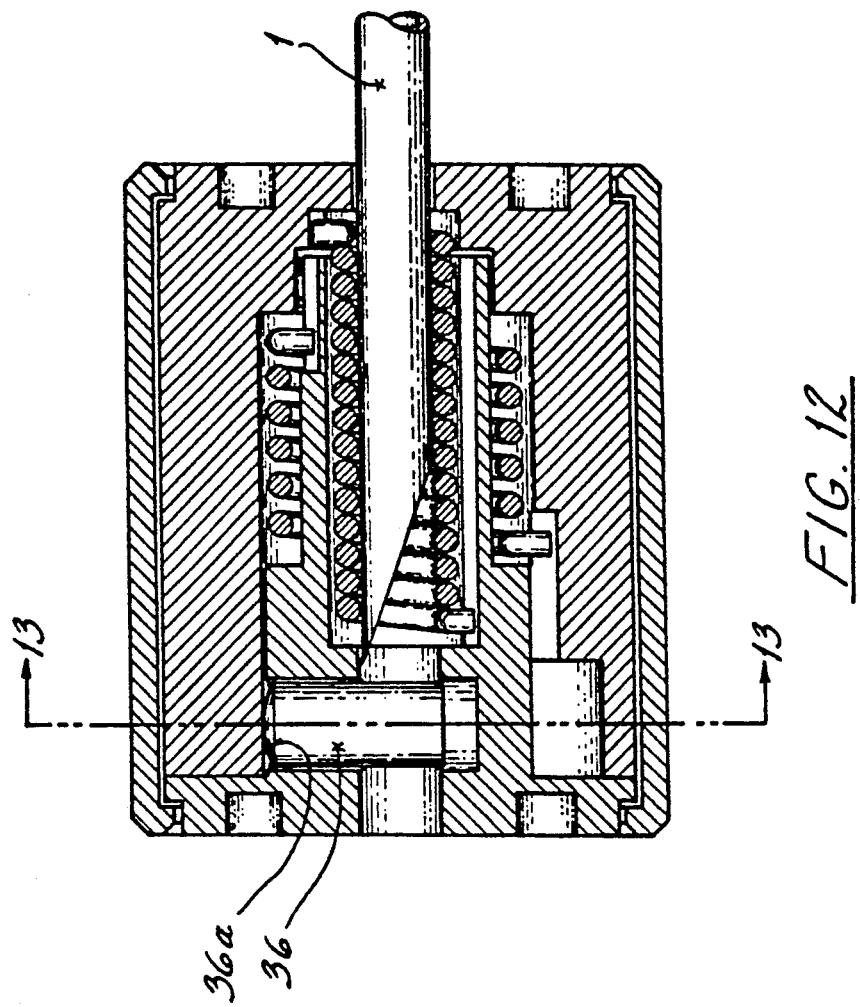
FIG. 12 shows the device of FIG. 10 with the end of the needle drawn inside the device, past the latch, and with the device locked onto the needle.
Figure 13:
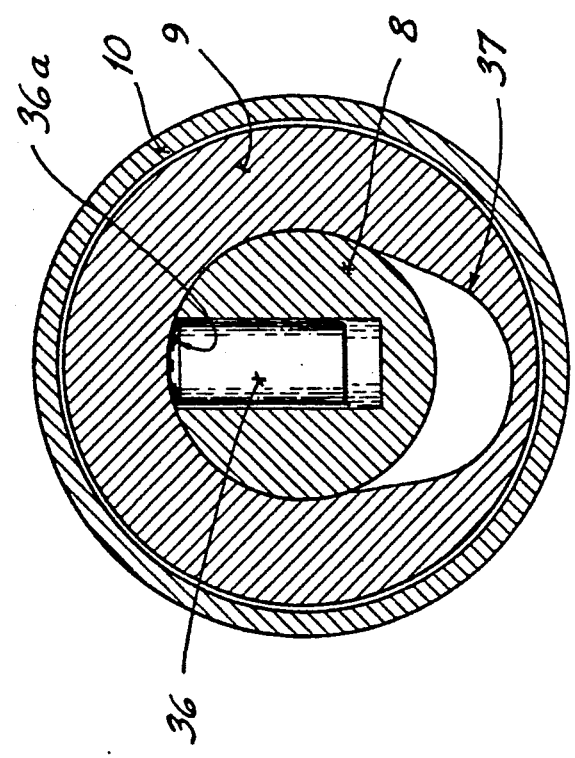
FIG. 13 is a cross sectional end view of FIG. 12, showing the principal latching components in the locked state.

4.2.27 In FIG. 12 the needle has been withdrawn into the body of the guard 5 until its tip has disengaged the inner end of locking plunger 36. This allows the plunger 36 to move radially inwards and thus permit the outer core 9 to rotate clockwise with respect to the inner core 8 as shown in FIG. 13. This allows the locking spring 16 to firmly grip the needle shah 1 and secure the guard 5 to the end of the needle, as described above.

4.2.28 In the locked state as shown in FIG. 12, the position of the plunger 36 blocks the tip of the needle 3 from re-emerging from the guard 5, in the same manner as described for the previous embodiment.

Figure 14:
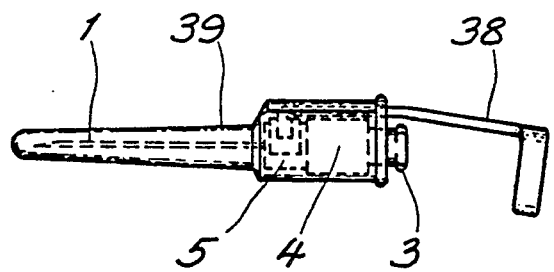
FIG. 14 shows an embodiment of the guard device in its protective sheath prior to use, this embodiment including a detachable handle on the guard device.

4.2.29 In instances where it is desirable to increase the separation between the operator's fingers and a possibly contaminated needle, a further embodiment provides a detachable handle to allow the operator to slide the guard device along the needle from a safe distance. FIG. 14 shows this embodiment, where detachable handle 38 is frictionally attached to guard 5, and the assembly of needle 1, guard 5, and handle 38 are encased in protective sheath 39, ready for use. The entry of protective sheath 39 is provided with a with a key-hole shaped cross-section to accommodate handle 38, and the other retaining features described above would also be included in the entry of this sheath.

Figure 15:
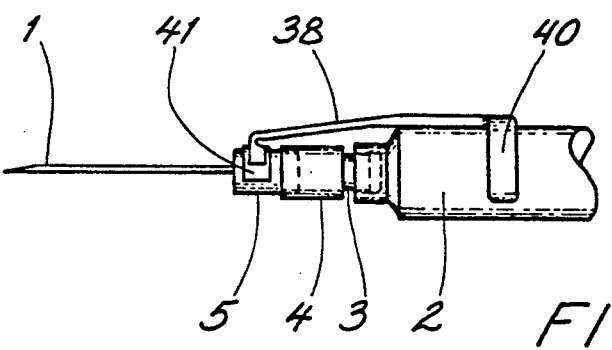
FIG. 15 shows the device of FIG. 14 removed from its protective sheath and mounted on a syringe, ready for use.

4.2.30 In FIG. 15, syringe 2 has been fitted to the needle connector or base 3, the circular clip 40 of handle 38 has been snapped over the body of syringe 2 for retention, and the needle and guard assembly has been removed from the protective sheath ready for use. Handle 38 is frictionally attached to guard 5 by circular clip 41.

Figure 16:
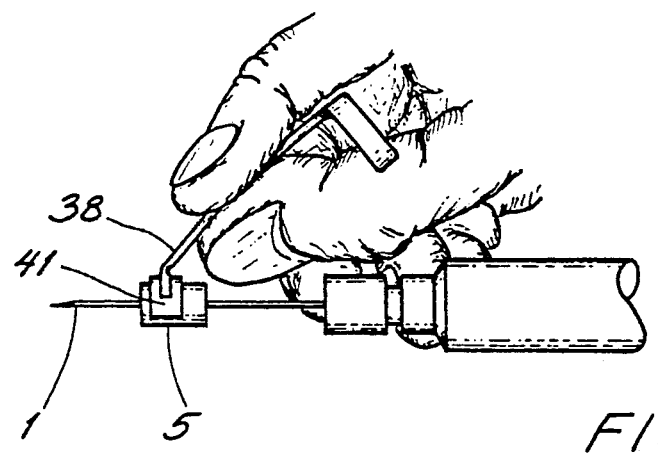
FIG. 16 shows the device of FIG. 15 following use of the needle, with the protective device being moved along the needle with the detachable handle.
Figure 17:
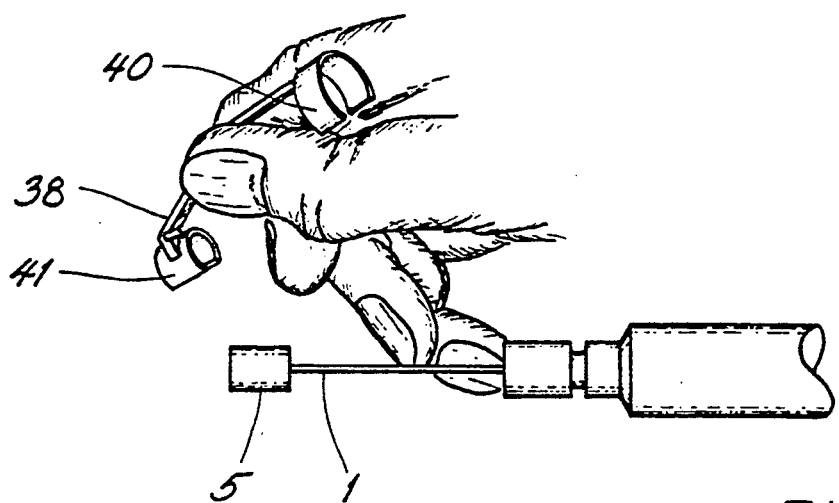
FIG. 17 shows the device of FIG. 15 with the protective device locked on the end of the needle and the detachable handle pulled free for disposal.

4.2.31 FIG. 16 shows guard device 5 being slid along needle shaft 1 following use, using handle 38. When guard 5 locks on the end of needle 1, handle 38 may be detached for disposal by pulling or twisting, as shown in FIG. 17.

4.2.32 An alternate embodiment of the invention may be constructed which relies on a locking system of the "push nut" type. The generally assembly of the components for this embodiment may be seen in exploded view FIG. 24 wherein a pair of locking leaf elements 51 are mounted on a rim 52 within a body 43, coaxially with the needle 1.

4.2.33 Referring to FIG. 18, latch shaft 42 is mounted transversely in the body 43. A portion of the left side of latch 42 is relieved to form a fiat surface 44 in the axial plane on either side of an unrelieved center portion 45, through which the needle shaft passes at fight angles to the latch axis, thus preventing its rotation in the body 43.

4.2.34 Sliding axially in the bore 46 of body 43 is pressure sleeve 47, in the form of a hollow cylinder, largely closed at the right end. A portion of its left half is cut away to form bifurcated arms 48 which engage the plane surfaces 44 of latch 42, thus preventing motion of the pressure sleeve to the fight when latch 42 is in the position shown.

4.2.35 Referring to FIG. 20, pressure sleeve 47 is pressed to the right by compression spring 49, whose leftwards reaction is taken by spring plunger 50, sliding freely within sleeve 47, and which presses against latch 42. The latter 42 holds plunger 47 away from the ends of locking leaves 51, which are retained in bore 46 by retaining rim 52, integral with leaves 51. The rim 52 is deflected out of its free form to produce a slight interference fit in bore 46, thereby allowing it to be retained at the bottom of the bore.

4.2.36 The locking leaf assembly is shown in FIG. 21, two leaves being shown in this example. Optionally one leaf or more than two leaves could be employed with equivalent results. In FIG. 20 spring pressure to the right on sleeve 47 is transmitted to the plane surfaces 44 of latch 42 by arms 48, the ends of which are radially separated from the axis of latch 42 by distance 53. This forms a small turning moment tending to cause rotation of the latch in a clockwise direction as viewed in FIG. 18, this rotation being prevented by the needle shaft passing through the axis of the latch.

Figures 22, 23:
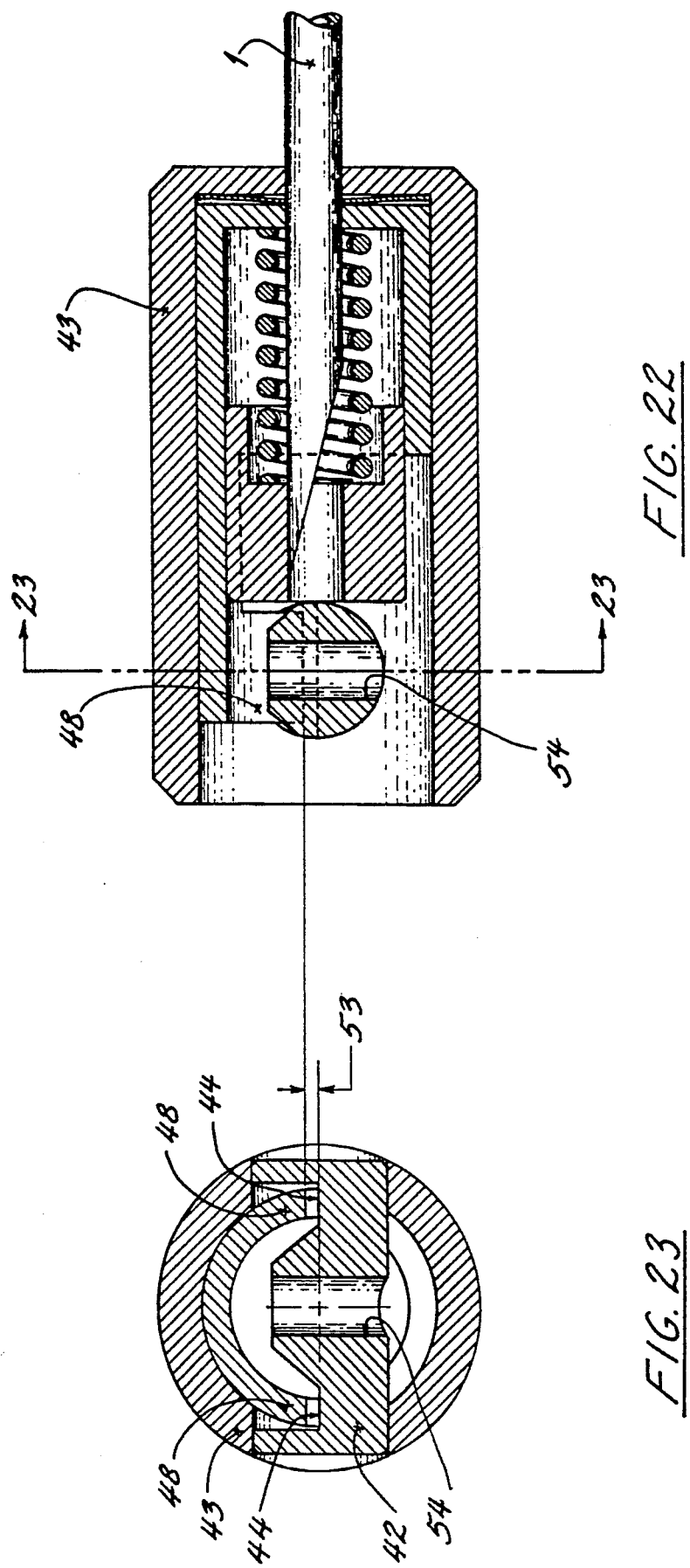
FIG. 22 is a cross-section of the device of FIG. 18 in its locked state.
FIG. 23 is a cross-section of FIG. 22 showing the latch in its locked position.

4.2.37 In FIG. 22, needle 1 has been withdrawn until its tip is inside body 43 and free of latch 42, allowing the latter to rotate until its plane surfaces 44 are parallel with the axis of pressure sleeve 47. This allows the latter to slide to the right past the latch and apply spring pressure to the ends of locking leaves 51, pressing them against the needle shaft 1. This locks the latter in position, preventing further motion to the right, relative to the body. The continued engagement of the arms 48 of sleeve 47 with the cut-away portions of latch 42 prevents the latter from falling out of body 43, and from rotating significantly about its own axis.

4.2.38 The needle is now prevented from withdrawing from body 43 to the right, and as latch 42 is now turned and locked in position with its needle held 54 at right angles to the needle axis, the needle point cannot re-emerge from the left end of the body, even though the one-way locking action of leaves 51 may permit motion in this direction.

Figure 25:
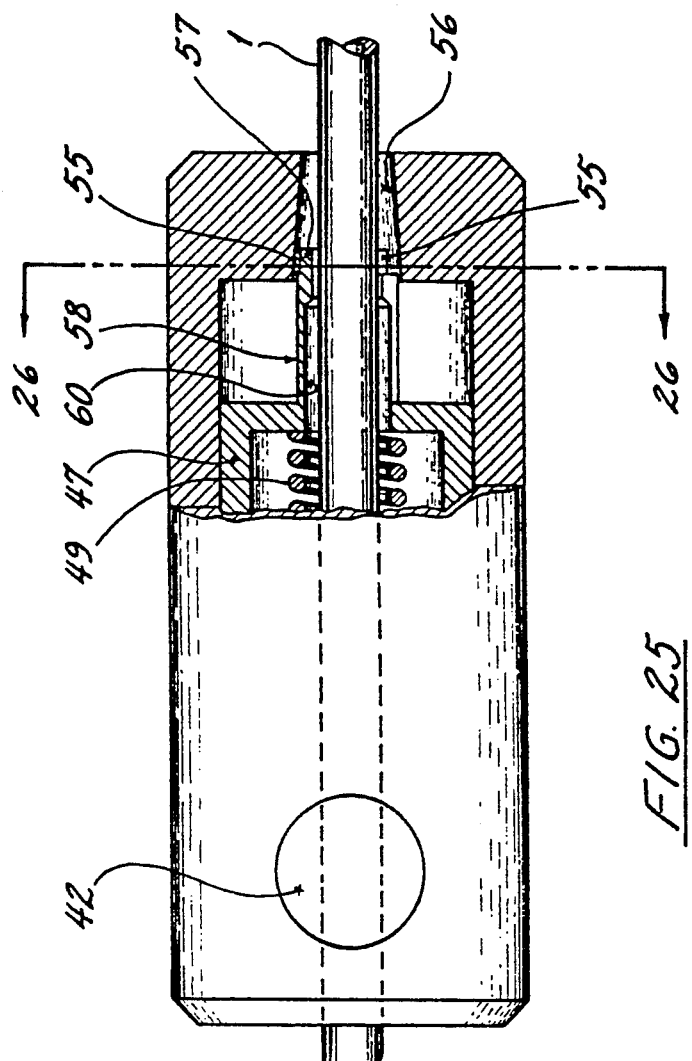
FIG. 25 is a partial cross-section of the device in the embodiment incorporating jaws within a chuck, shown in its unlocked state.
Figure 26:
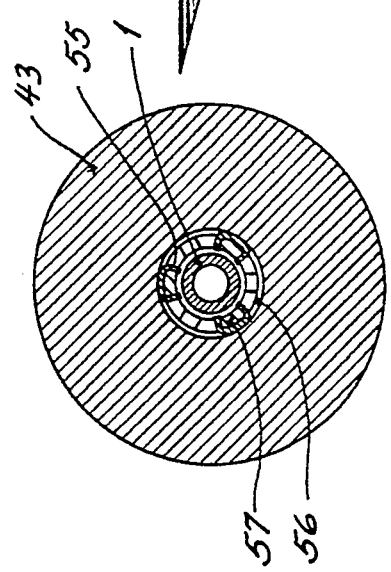
FIG. 26 is a cross-section of FIG. 25 showing an end view of the locking jaws, viewed from within.
Figure 27:
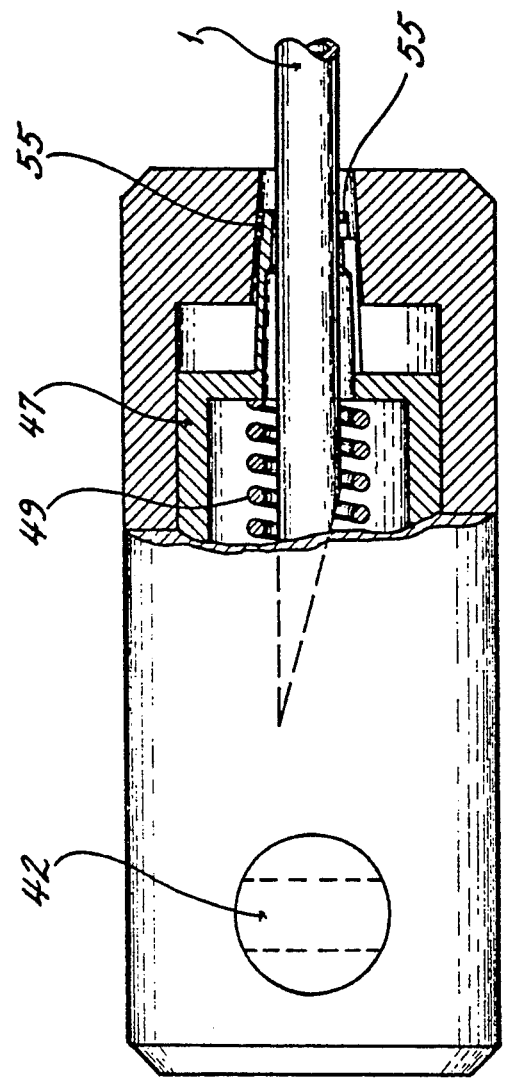
FIG. 27 is a partial cross-section showing the device of FIG. 25 in its locked state.
Figure 28:
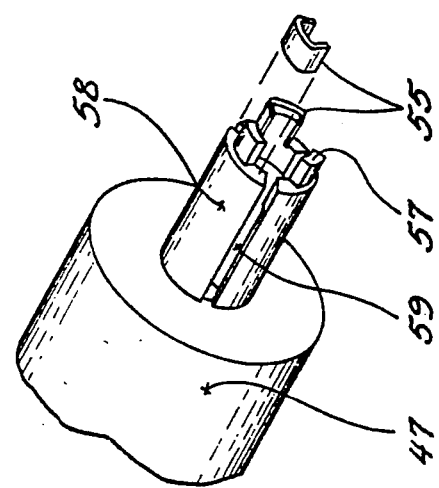
FIG. 28 is a perspective view of the device of FIG. 25 showing the locking jaws and their means of retention.

4.2.39 A third alternate embodiment is shown in FIG. 25 wherein the general locking means comprises three locking jaws 55 contained in a gently tapered conical cavity in the form of a bore 56 in the chuck body 43. In this example, these jaws are formed from sheet material into an approximately C-shaped cross-section and then hardened although alternate forms may be used. These are arranged uniformly about the needle shaft as shown in FIG. 26, and are retained loosely in this position by fingers 57 extending axially from the end of pressure sleeve 47, and fitting inside the jaws 55. This is shown in FIG. 28, one jaw being omitted for clarity.

4.2.40 Fingers 57 extend from a reduced portion or spigot 58 of pressure sleeve 47, to allow entry of the latter into bore 56 during locking. This spigot is provided with axial slots 59 as shown in FIG. 28 to allow its outer end to collapse slightly in diameter as it is forced into the tapered bore 56. Further elasticity is imparted to this spigot bore 6121, shown in FIG. 25, by a reduction in its wall thickness in the vicinity of its junction with the main body of the pressure sleeve 47. A greater wall thickness is retained at its outer end where it presses against the locking jaws 55.

Figure 24:
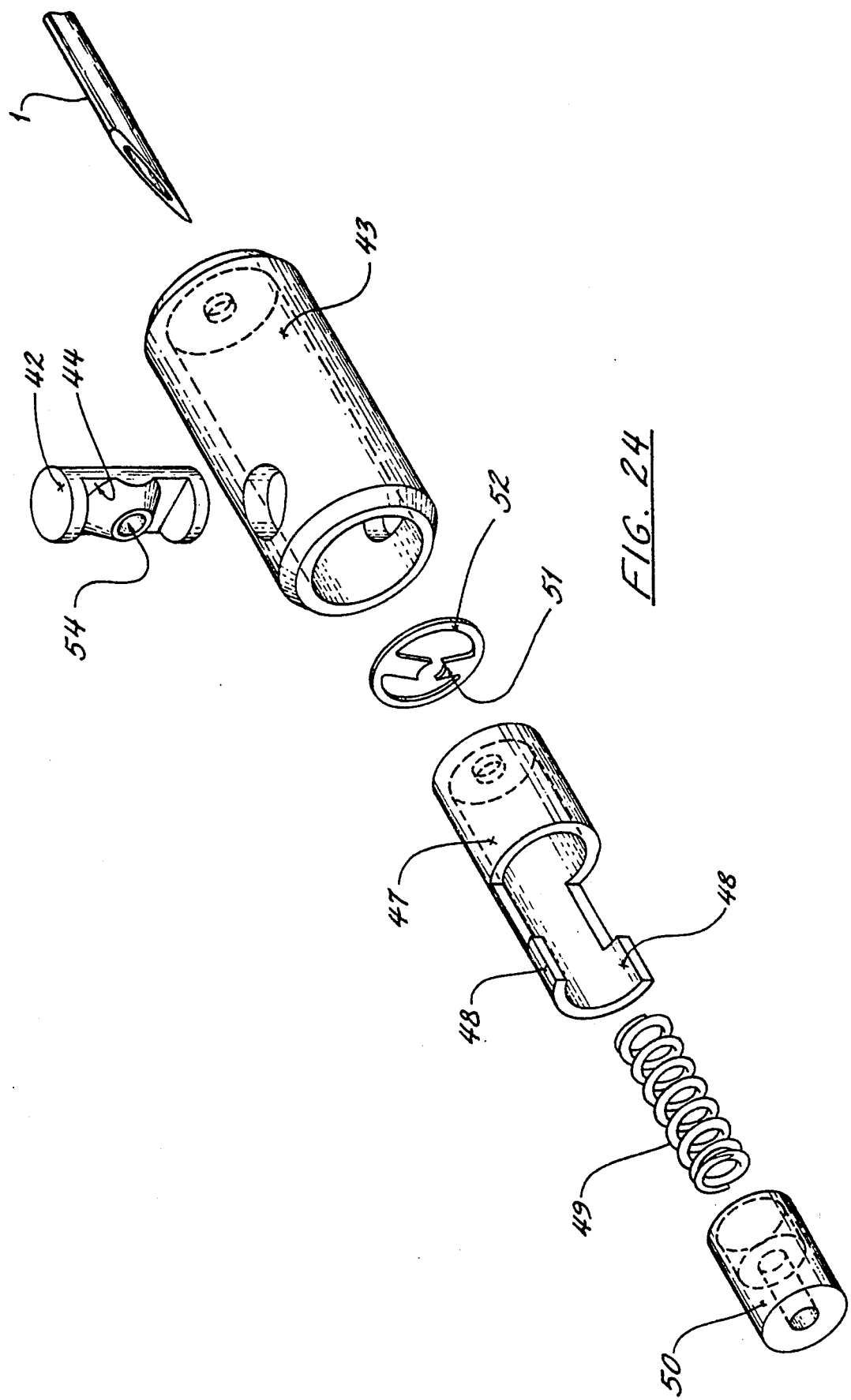
FIG. 24 is an exploded perspective view of the device of FIG. 22.

4.2.41 In the locked state, pressure sleeve 47 is released by latch 42 as in FIG. 24 and its spigot drives jaws 55 into the narrowing annular space 56 between the needle shaft 1 and the tapered bore 56, forcing the jaws 55 against the needle shaft 1. Contact between the two is made along the narrow rectangular edges of the C-shaped jaws 55. By finely serrating these edges in the blanking stage of forming the jaws, the coefficient of friction between jaw and needle shaft may be substantially increased.

4.2.42 By providing a suitable length of tapered bore 56, this clamping means can accommodate a range of needle diameters.

4.2.43 A fourth alternate embodiment is shown in FIG. 29, wherein the general locking means comprises a plurality of locking rollers 61 of hardened material, two being shown in this example. These are loosely contained in an axially tapering cavity 62 of substantially rectangular cross-section in the body 43 of the guard device. Each locking roller 61 is loosely retained within a substantially rectangular cavity 63 in a rectangular extension 64 of pressure sleeve 47, with the axis of each locking roller 61 in a common plane perpendicular to the axis of the needle shaft 1, and with each roller 61 uniformly disposed about the axis of needle shaft 1, as shown in FIG. 30.

4.2.44 In the unlocked state, the pressure sleeve 47 is held by the latch 42 against the pressure of the spring 49 as described above, such that the locking rollers 61 are held loosely by extension 64 in the larger portion of the tapered cavity 62, making no significant contact with the walls 65 of the cavity 62 or with the needle shaft 1. In this state, the needle shaft 1 is free to move both axially and rotationally within its bore 92 in the guard device.

4.2.45 In the locked state, as shown in FIG. 29, the latch 42 releases the pressure sleeve 47 by the same action as in FIG. 24 to move under pressure of spring 49 towards the narrowing end of cavity 62 as described above, so that extension 64 carries the locking rollers 61 into contact with the wall 65 of the tapering cavity 62 on the outside and the needle shaft 1 on the inside. Motion of the needle shaft 1 relative to the body 43 in the same direction as the spring directed motion of pressure sleeve 47 will cause the locking rollers 61 to roll further into the gradually narrowing end of cavity 62, exerting a high radial pressure against the wall 65 and the surface of the needle shaft 1. This prevents further motion of the needle by frictional grip between the rollers 61, the cavity walls 65, and the needle shaft 1.

4.2.46 By providing a suitable length of tapered cavity 62, this clamping means can accommodate a range of needle diameters from any arbitrary maximum value down to zero.

4.2.47 A fifth alternate embodiment is shown in FIG. 32, wherein the general locking means comprises a plurality of locking balls 66 of hardened material, three being shown in this example, as more clearly seen in FIG. 30. The balls 66 are loosely contained in an axially tapering bore 67 of circular cross-section in the body 43 of the guard device. Each locking ball 66 is loosely retained within a cage optionally composed of a substantially cylindrical cavity 68, the axis of each said cavity being perpendicular to the needle axis in a cylindrical extension 69 of pressure sleeve 47. The center of each locking ball 66 lies in a common plain perpendicular to the axis of the needle shaft 1, and the balls 66 are disposed uniformly about the needle shaft 1, as shown in FIG. 33. In all other respects, the action of the locking balls 66 in the locked state is similar to that of the locking rollers 61 as described above.

4.2.48 By providing a suitable length of tapered bore 67, this clamping means can accommodate a range of needle diameters from any arbitrary maximum value down to a minimum diameter determined by the point at which the locking balls come into contact with one another. When three balls are used, this minimum needle diameter theoretically approximately 0.155 of the diameter of the locking balls. Considerations relating to the retention of the locking balls place a practical limit of approximately 0.3 of the ball diameter. The minimum diameter of needle which can be gripped becomes progressively larger as more than three balls of a given size are used.

4.2.49 Thus three alternate embodiments have been described which rely on narrowing cavity to achieve the locking effect. The latch and trigger mechanism described for each case has been of the transverse rotating cylinder class. An alternate latch and trigger system could be substituted, relying, for example, on the next described sensing pin or lever arm types of systems.

Figure 39:
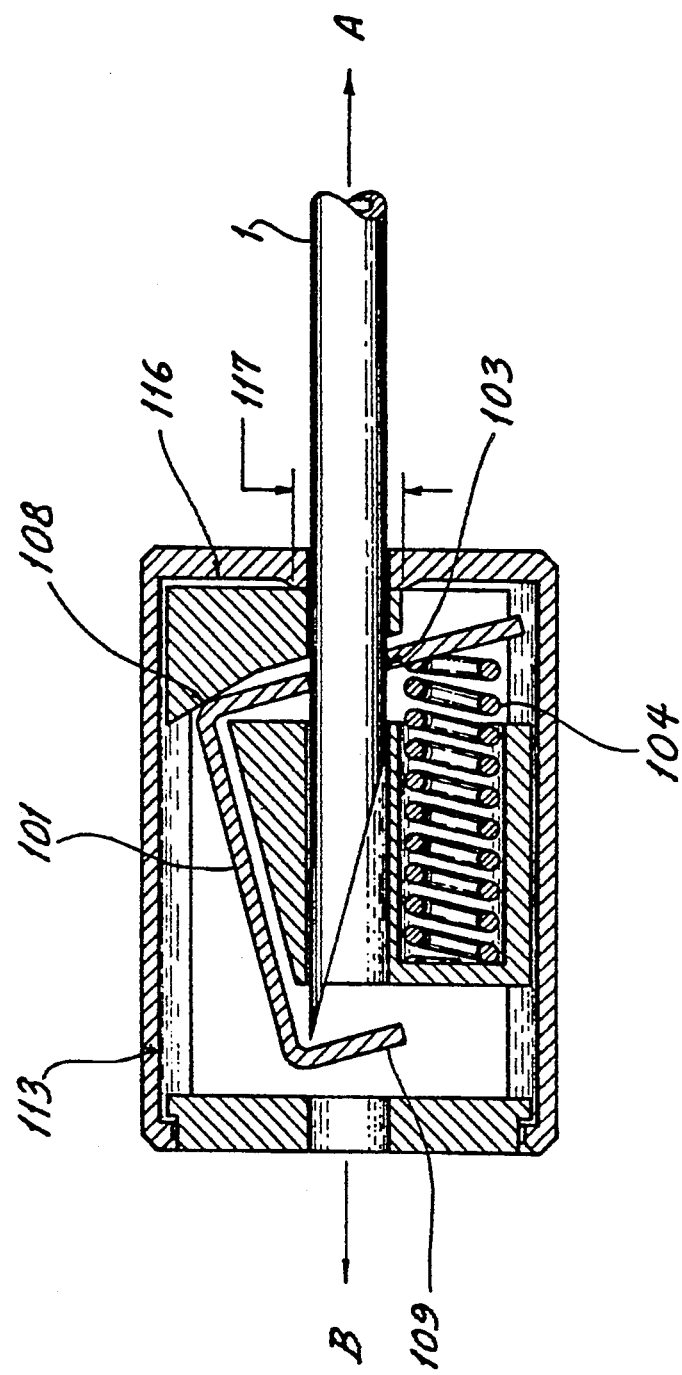
FIG. 39 is a longitudinal cross-section of the device showing the relationship of the parts in the locked state.

4.2.50 A sixth embodiment is shown in FIG. 35, wherein the general locking means comprises a pivoting or lever arm or lever 101 of stiff material, formed in the general shape of a broad U of unequal proportions, with the longer vertical leg 102, referred to as the locking plate 102, provided with a hole 103 of slightly larger diameter than that of the needle shaft 1 sufficient to allow the locking plate 102 to "cant" on the needle 1 as shown in FIG. 39. This hole 103 is also shown in cross-sectional view FIG. 36.

Figure 38:
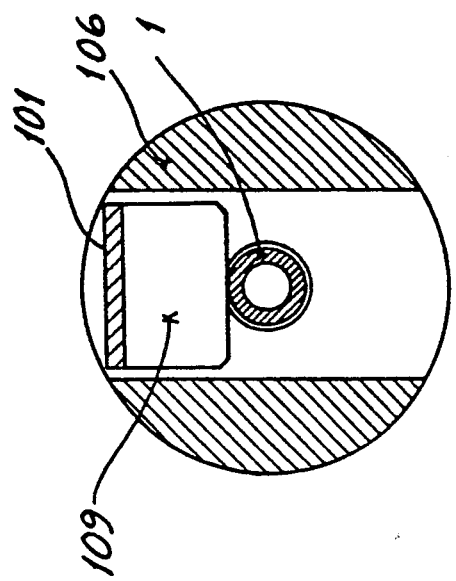
FIG. 38 is a cross-sectional view showing the latch portion of the lever in contact with the needle shaft in the unlocked state.
Figure 37:
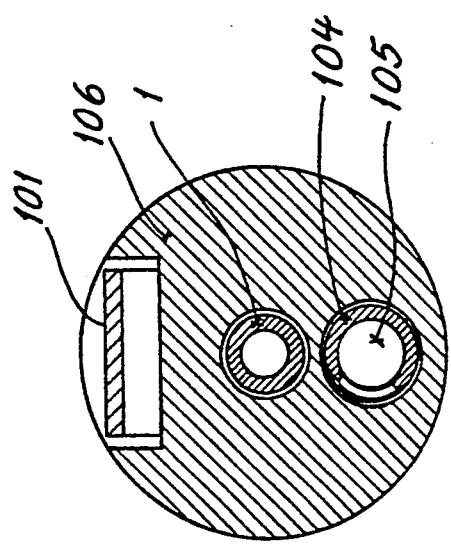
FIG. 37 is cross-sectional view showing the needle and spring contained within the mid-portion of the body of the device.

4.2.51 A helical compression spring 104, also shown in simplified cross-sectional view FIG. 37, is contained in a largely compressed state in longitudinal cavity 105 within the guard body 106, with its free end 125 pressing against the locking plate; 102 of lever 101, and urging the lever 101 axially against the sloping internal face 107 of body 106, making contact at pivot point 108. The turning moment of the spring force tends to rotate lever 101 in a counter-clockwise direction about pivot point 108, but the shorter vertical leg 109 of lever 101, referred to as the latching or locking leg, prevents rotation by making contact with the needle shaft 1 at point 110. This is shown also in simplified cross-sectional view FIG. 38.

4.2.52 By appropriate choice of the slope of face 107 in relation to the geometry of lever 101, a component of reaction force will be developed to act at pivot point 108 in a downward direction against lever 101, equal and opposite to the upward reaction force against the lever at point 110. This balancing of vertical forces against lever 101 substantially removes any radial force between nee, die shaft 1 and the walls of hole 103 in lever 101, thereby reducing axial frictional drag between the needle and lever when moving the guard device axially along the needle shaft.

4.2.53 In FIG. 39 the needle shaft is shown withdrawn into the guard and past the point of contact with the sensing end of locking leg 109 of lever or pivot arm 101. This allows lever 101 to rotate in a counter-clockwise direction about pivot point 108 under the urging of spring 104, which rotates the locking plate 102 until further rotation is prevented by the axial misalignment of hole 103 and needle shaft 1.

4.2.54 By utilizing well-known relationships between the thickness 111 of latch 101, as shown in FIG. 35, the distance 112 between the pivot point 108 and the centre of the needle shaft 1, the diameter of hole 103, the diameter of needle shaft 1, and the coefficient of friction between latch 101 and needle shaft 1, a critical geometry is established, whereby the axial frictional grip between lever 101 and needle shaft 1 is always greater than the externally-applied axial force on the needle in the direction "A" relative to the guard device. Thus further motion of the needle shaft in this direction is prevented by the locking of plate 102 on needle shaft 101, its axial motion with respect to the guard body 106 being blocked by sloping face 107. With increasing applied axial force in direction "A", this locking action will persist until material deformation occurs, distorting the geometry beyond the critical configuration.

Figure 52:
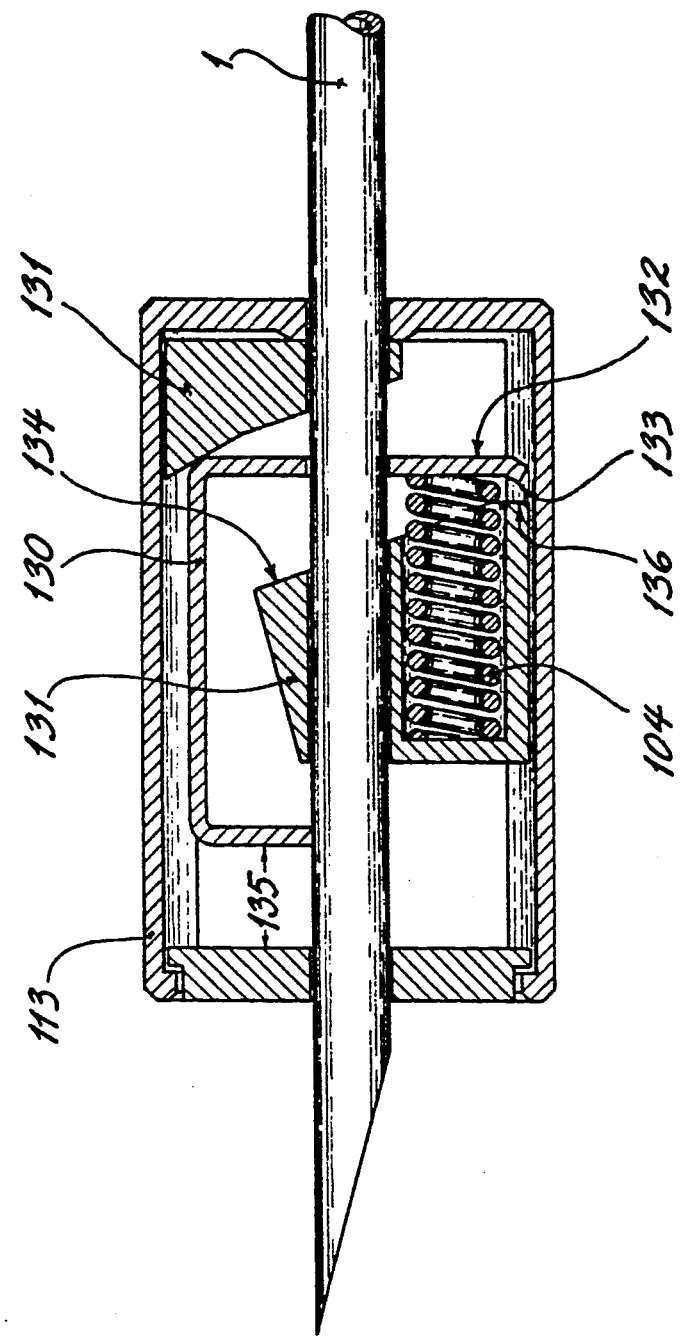
FIG. 52 is an alternate version of the embodiment of FIG. 35, in an unlocked state.
Figure 53:
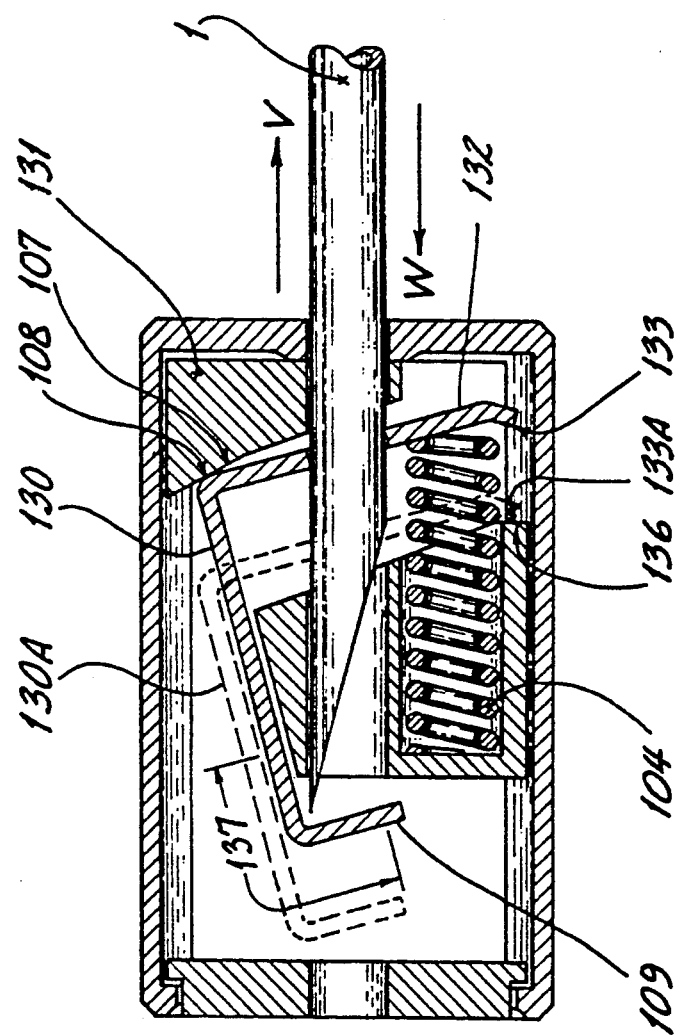
FIG. 53 shows the embodiment of FIG. 52 in a locked state.

4.2.55 This locking action is released if the relative needle motion is reversed to direction "B", by attempting to slide the guard device back onto the needle. However, such motion is blocked by the presence of latching leg 109 in the return path of the needle, preventing re-exposure of the needle point by a substantial obstruction of hardened material. Alternately, as shown in FIGS. 52 and 53, a complementary pivot point 136 may be provided on the guard body 106 adjacent and on the outward side of the spring 104. This pressure point 136 is located so as to apply a canting force to a modified locking plate 132 through a contacting flange 133 at the end of the locking plate 132 when the needle is moved in direction for re-emergence of the tip, as shown in FIG. 53 thus locking the guard body 106 against removal in this direction as well. On initial displacement towards re-emergence, the needle, will carry the lever arm 130, forward until the contacting flange 133 rests against the complementary pivot point 136, identified in this position as 133A. Any further attempt at displacement will apply the same canting force to the locking plate 132. As a further modification over the embodiment of FIG. 35, the guard body 131 of FIG. 53 is lengthened to provide clearance space 132 for the additional displacement of lever arm 130. Additionally, the surface 134 on the interior body portion 131 is inclined to provide freedom for the locking plate 132 to become canted.

4.2.56 To prevent the guard device from being removed forcibly from the needle by its repeated rotation about the needle shaft, the body 106 is preferably surrounded by loosely-fitting sleeve 113, which provides rotational isolation of the body 106 from the external operating means. Sleeve 113 is retained axially on body 106 by snap lips 114, fitting into a circular rabbet 115 in one end of the body. Referring to FIG. 39, the inner face 116 of sleeve 113 is relieved over most of its surface to make axial contact with body 106 only over a small diameter 117. This reduces the frictional torque transmitted between sleeve 113 and body 106 by combined axial and rotational force applied to the guard device by the external operating means, thus enhancing its rotational isolation.

Figure 40:
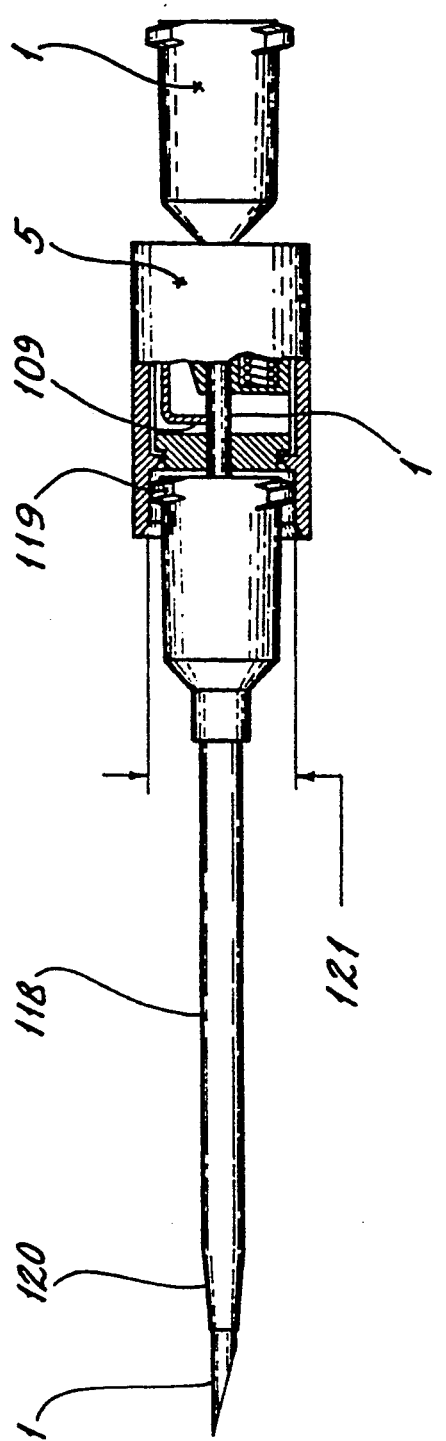
FIG. 40 shows the guard device of FIG. 39 fitted to an intravenous catheter assembly, prior to insertion into a patient.

4.2.57 FIG. 40 shows the protective guard device 5 fitted to a needle 1 and attached to a catheter 118 as part of an intravenous catheter assembly. The embodiment of FIG. 35 is shown here as an example but any other embodiment could be similarly employed. The outer shell 113 of the guard extends over and is frictionally retained on the tubing attachment chuck 119 or base of the catheter 118. The needle 1 extends through the guard 5 and the catheter 118 to emerge slightly beyond the distal end 120 of the catheter. The needle may be moved freely within the catheter 118 in any direction, either axially or rotationally, impeded only by the slight drag of the latch 109 of guard 5 and the constriction of the reduced end 120 of the catheter tube 118.

Figure 41:
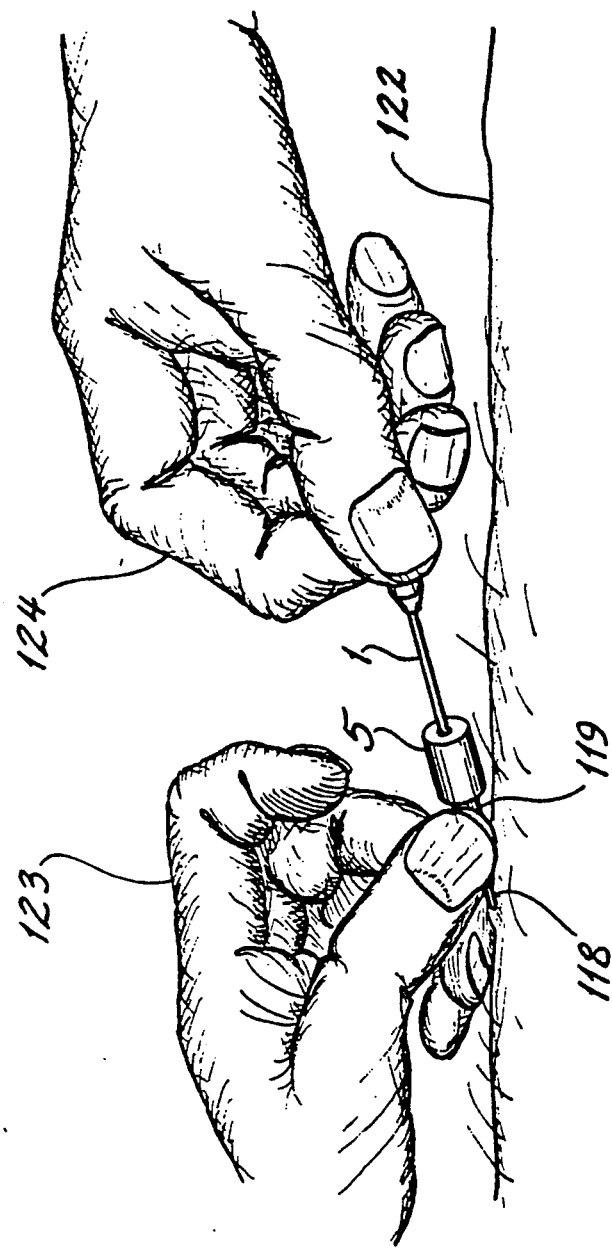
FIG. 41 shows the catheter inserted into a patient with the guard in place on the catheter and the needle being withdrawn

4.2.58 The inner diameter 121 of the extended portion of shell 113 is such as to provide a frictional axial retention force between shell 113 and catheter chuck 119 significantly greater than the maximum axial drag of needle 1 within guard 5, and comparable to the initial axial retention familiarly encountered between the needle and catheter in a conventional intravenous catheter assembly. This retains guard 5 on catheter chuck 119 during needle withdrawal, as shown in FIG. 41. Here the operator has inserted needle 1 and catheter 118 into a blood vessel in the patient 122, and is withdrawing needle 1 from catheter 118 through guard 5, holding catheter 118 in place with one hand 123 and holding needle 1 with the other hand 124. The guard 5 remains frictionally retained on chuck 119 of the catheter.

Figure 42:
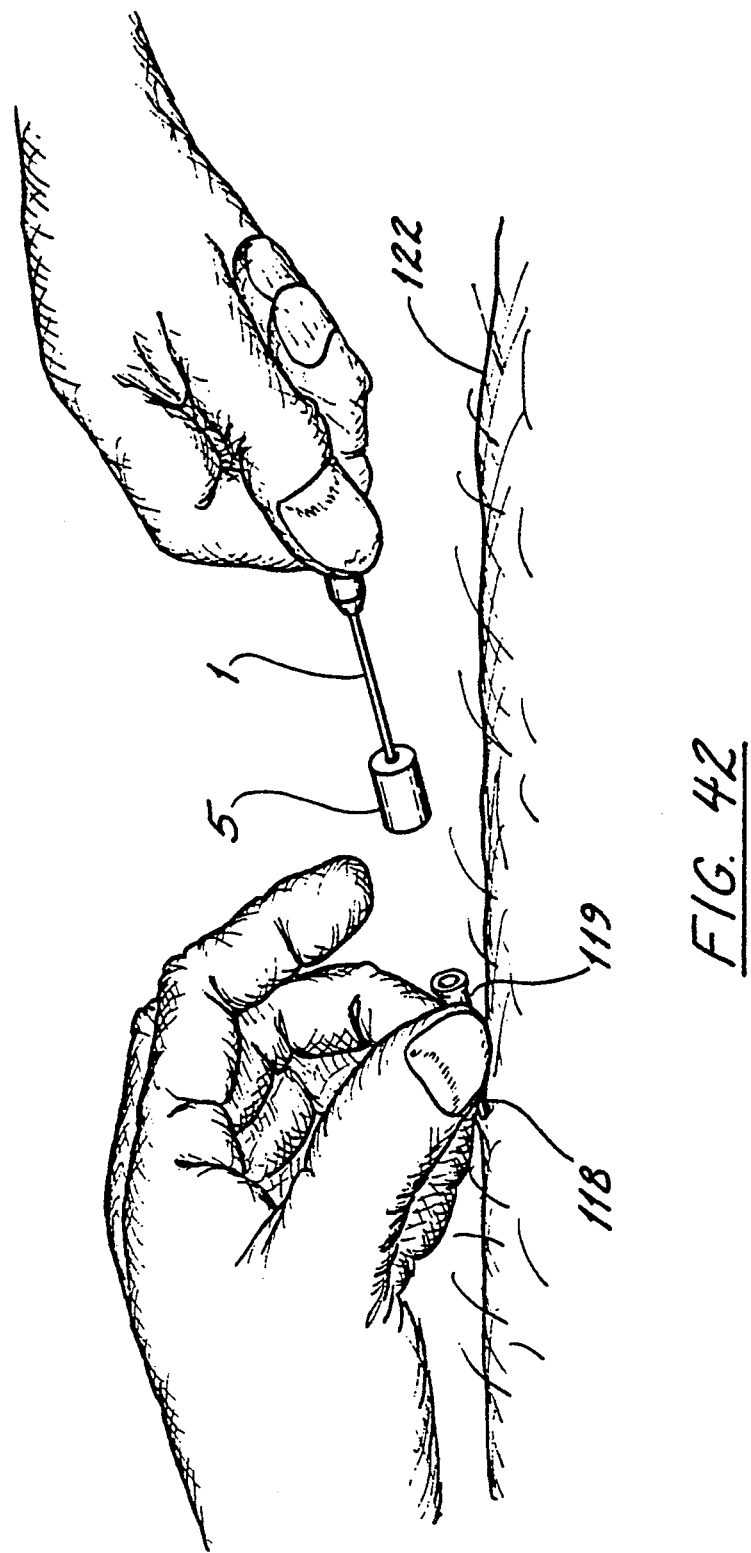
FIG. 42 shows the needle fully withdrawn from the catheter with the guard locked over the point of the needle.

4.2.59 When the needle point passes the latching leg 109 and the guard 5 locks automatically onto needle shaft 1, the operator exerts a slightly increased withdrawal force on the needle, sufficient to release guard 5 from catheter chuck 119, as shown in FIG. 42. The operator can now dispose of the protected needle without further action, while attending to the catheter tube attachment.

4.2.60° A seventh embodiment is shown in FIGS. 43 to 51. This version relies on a ball-latching mechanism to main the guard in a cocked condition, and a sensing-ball arrangement to serve as the trigger. This embodiment is shown in a form adapted to be installed on a catheter assembly. It could equally be applied to a straight needle, as used on a syringe.

4.2.61 Prior to use, the needle guard assembly FIG. 43, 43-51, inclusive, is housed largely within the base of the catheter 209. The guard base 201 provides radial support for the base 210 of the needle 1 but does not fictionally retain it axially. The guard shell 202, which is retained on guard base 201 by snap-fit shoulders 212, has an outer surface tapered to fit the correspondingly tapered bore 213 of the catheter base 209, with moderate axial frictional retention therein.

4.2.62 During insertion of the catheter, the necessary axial thrust is transferred from the face 214 of the needle base 210 to the guard base 201 and thence through face 215 of the latter to catheter base 209, without affecting the respective radial fits described in para 2.4.61 above.

4.2.63 During withdrawal of the needle from the catheter, the needle base 210 readily releases from the guard base 201, while the latter is axially retained within the catheter base 209 by the greater frictional grip between the two, per para 2.4.61 above.

Figure 43:
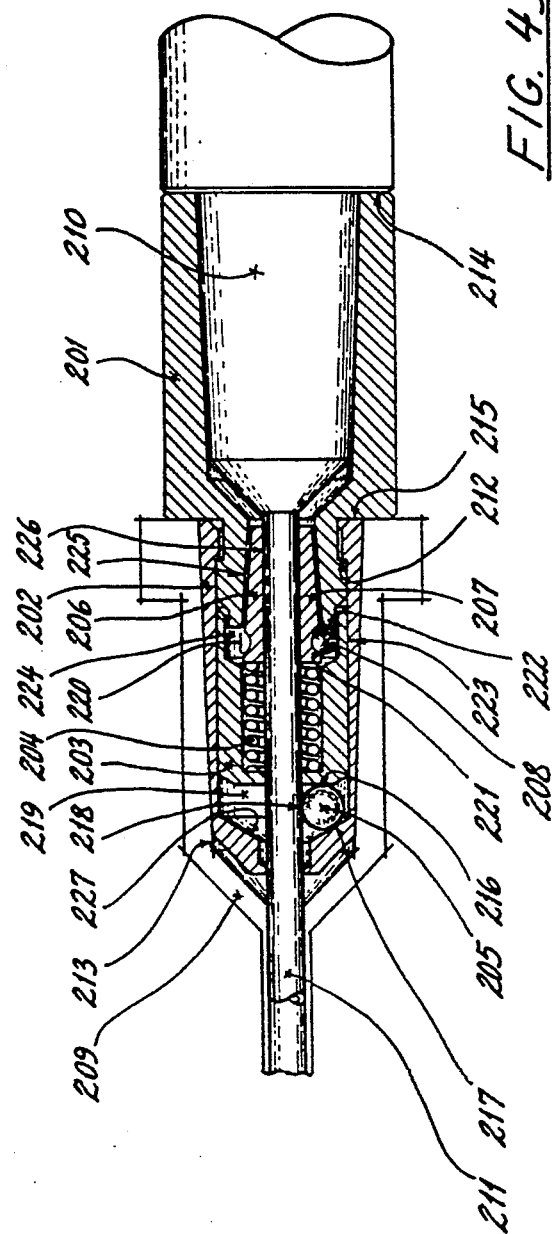
FIG. 43 shows a catheter with needle protector based on a double trigger mechanism utilizing on a ball-latch and sensing ball system, in cocked condition.

4.2.64 With the needle 211 passing wholly through the needle guard assembly as in FIG. 43, interval plunger 203 is urged towards the pointed end of the needle 211 by compression spring 204, but is prevented from moving axially by the three-point confinement of sensing ball 205, which makes contact with plunger 204 against the latter's perpendicular end face at point 216, against the sloping internal end face 227 of guard shell 202 at point 217, and against the needle shaft 211 at point 218. The sensing ball 205 is free to move orbitally about the needle axis in the annular space 219 surrounding the needle.

4.2.65 The reactionary force at the opposite end of spring 204 acts against the perpendicular end face of the pair of locking jaws 206 and 207, but motion of these latter parts is prevented by the confinement of latching ball 208. This makes contact with jaw 207 on the curved side of its guard 220 at point 221, with the perpendicular end face of guard base 201 at point 222, and with the cylindrical inner surface of plunger 203 at point 223. Axial motion of locking jaw 206 is prevented by its being axially locked to jaw 207 as will be described below. Latching ball 208 is free to move orbitally about the needle axis in the annular space 224 surrounding locking jaws 206 and 207.

4.2.66 With jaws 206 and 207 held axially as shown in FIG. 43, their tapered outer surfaces are confined within the correspondingly tapered inner bore 225 of guard base 201 to an extent sufficient to radially support the needle shaft 211 on the cylindrical inner surfaces 226 of the locking jaws, yet without developing sufficient frictional contact to significantly impede the axial movement of the needle shaft through the jaws.

4.2.67 Similarly, the pressure of plunger 203 against sensing ball 205 is re-directed by contact point 217 to produce a reduced force at contact point 218, such that the frictional force between the polished surfaces of sensing ball 205 and needle shaft 211 negligibly impedes the axial movement of the needle shaft 211 within the needle guard.

4.2.68 As the point of the needle enters the needle guard during withdrawal, sensing ball 205 passes over the end of the needle, following the inclined inner end face 227 of body shell 202, under the axially-directed urging of plunger 203, driven by spring 204. The greatest extent of this motion before the sensing ball 205 becomes free of the needle occurs with the bevel 228 of needle 211 rotationally oriented to be tangent with the surface of ball 205 as shown in FIG. 44, and with the point of tangency 229 being on the end of a line passing through the centre of the sensing ball 205 to an opposite point of contact 230 between the sensing ball 205 and the corner of ball socket 231 in the end of guard shell 202.

Figure 44:
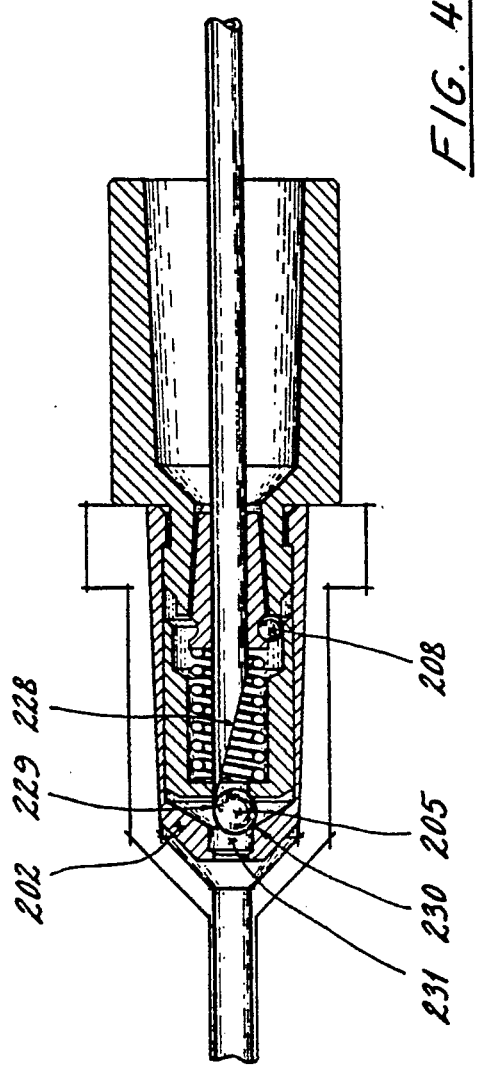
FIG. 44 shows the device of FIG. 39 in transition to grasping the needle.

4.2.69 It will be seen that the configuration in FIG. 44 is a critical one, in that reversal of the needle withdrawal motion will not cause the ball to likewise reverse its motion towards the configuration of FIG. 403, because the force exerted on the ball by the tangential face 228 of the needle acts on a line through the centre of the ball, and therefore cannot move it in any direction. It will be seen further that when the configuration of FIG. 44 is reached, the spring-driven plunger 203 will force sensing ball 205 free of the needle 211, and drive it into ball cavity 231, as shown in FIG. 45.

4.2.70 With the configuration of FIG. 44, the geometry of the containment of latching ball 208 is the same as in FIG. 43, so that the locking jaws 206 and 207 cause no significant resistance to the axial motion of the needle 211, yet continue to provide radial support to it. Thus the withdrawal motion of the needle 211 can continue beyond the critical configuration of FIG. 44, ensuring that sensing ball 205 is released into its cavity 231 to block the re-emergence of the needle point, before the locking jaws 206 and 207 are activated.

4.2.71 When the plunger 203 moves to the position of FIG. 43, it releases latching ball 208 from the confinement of FIGS. 43 and 44, allowing locking jaws 206 and 207 to be driven by spring 204 into the confinement of tapered bore 225 in guard base 201. This causes the jaws 206 and 207 to grip the needle shaft 211. The angle of taper of bore 225 is critically selected with respect to the coefficients of friction between the jaws 206 and 207 and needle shaft 211 and between the jaws and bore 225, such that the axial component of frictional grip between the jaws and the needle shaft is always greater than the externally-applied axial force on the needle, which develops this gripping force. Thus the needle cannot be withdrawn from the needle guard, as the gripping force of the jaws on the needle increases with withdrawal force until material failure occurs. Re-emergence of the needle is resisted to a much lesser degree by the locking jaws 206 and 207, but such re-emergence is blocked by the sensing ball 205 which now blocks the exit path of the needle 211 from the guard.

4.2.72 The self-locking action of the jaws in the direction of withdrawal of the needle from the guard is independent of the axial force on the jaws of spring 204, and the latter acts only as the initiator of the locking action, by moving the jaws onto the confinement of tapered bore 225. Once in this position application of further withdrawal force on the needle 211 enhances the locking effect of the jaws 206 and 207 as they are drawn deeper into the narrowing cavity of the tapered bore 225.

4.2.73 The rotational component of the coefficient of friction between locking jaws 206 and 207 and bore 225 is significantly less than the rotational component of the coefficient of friction between the locking jaws and needle shaft 211. This maintains the rotational grip between the locking jaws and the needle shaft if the latter is rotated with respect to the nee, die guard, with relative rotation occurring between the locking jaws and bore 225.

4.2.74 The locking jaws 206 and 207 are shown in enlarged views FIGS. 46 to 50. The two jaws are identical, each having a substantially rectangular lug 234 extending from its diametral place on one side of its central axis, which engages a corresponding substantially rectangular recess 235 in the opposite jaw when the two are placed together on a common diametral place. The resulting engagement of each lug and recess prevents relative axial reaction of the two jaws. This allows the use of a single latching ball 208, as described above, holding the two jaws as an axially-coupled pair in the unlocked position.

4.2.75 The tapered outer surface 232, FIG. 46, is polished to reduce the coefficient of friction between the jaw and the bore 225 of the guard body 201.

Figure 51:
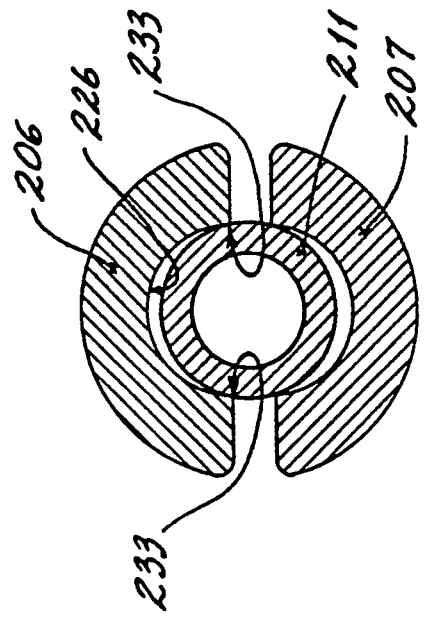
FIG. 51 is an end view cross-section of the jaw element of FIG. 43 as it embraces a needle.
Figure 50:
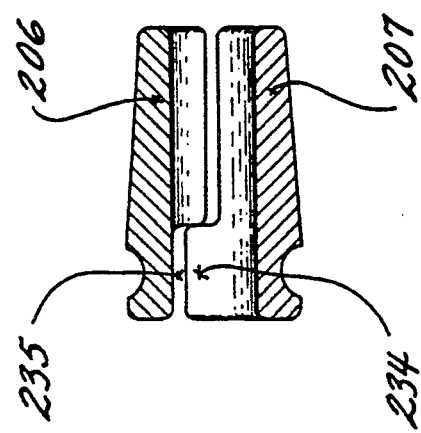
FIG. 50 is a side view cross-section through FIG. 43.
Figure 49:
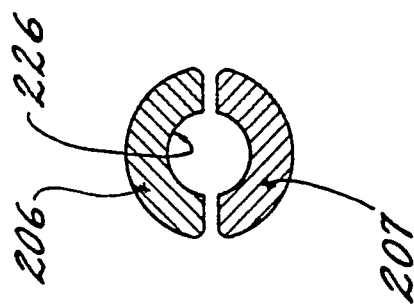
FIG. 49 is an end view cross-section through FIG. 44.

4.2.76 The internal bore 226, FIG. 49, is provided with a relatively coarse surface finish, and is furthermore of a slightly smaller diameter than that of the needle shaft 211. This produces contact with needle shaft 211 along axial lines of concentrated pressure 233, as shown in FIG. 51. This causes the exclusion of any bodily fluids which may be on the surface of the needle, and provides a high frictional grip both axially and rotationally.

4.2.77 This last embodiment demonstrates the use of a narrowing-cavity or chuck-action clamping system, in combination with a sensing ball trigger mechanism. A second latching ball is also employed to maintain the guard in its cocked condition. The major components in this embodiment may be readily manufactured by injection molding without onerous tolerance requirements, and this design has the capacity of having one size fit a range of needle diameters.

4.2.78 All of the principal parts of the device may be made of any suitable material, such as of injection moulded plastic, e.g. Nylon, or of corrosion-resistant metal such as stainless steel, according to such considerations as convenience of manufacture; cost and other factors relevant to medical devices.

4.2.79 Throughout the foregoing disclosure a hollow hypodermic needle has been depicted. The needle need not, however, be hollow. The protective guard contemplated by this invention is equally applicable to solid needles, such as might be used for smallpox inoculations.

4.2.80 The foregoing has constituted a detailed description of specific exemplary embodiments of the invention. The invention in its most general and more specific aspects is more particularly described and claimed in the claims which now follow.

We claim:

1. A needle tip protecting device for covering the tip of a needle comprising:
   (i) a body having an interior cavity;
   (ii) a locking plate positioned within said cavity, said locking plate having an opening therethrough, said opening being pierced by said needle with a close, sliding fit;
   (iii) alignment means to maintain said opening and said needle in sliding alignment while the needle tip is outside of said protecting means; and
   (iv) canting means to cant said locking plate into locking engagement with said needle against further removal from the needle when said tip enters within said body.

2. A needle tip protecting device for covering the tip of a needle having a smooth, continuous featureless outer surface adjacent the tip end thereof comprising:
   (a) a body with a needle passageway therethrough, for positioning the shaft of the needle to slide axially therein, said body being adapted to be mounted on and slidingly supported by said needle;
   (b) needle engagement means moveably distinct from but supported by said body for automatically engaging with a featureless portion of the surface of said needle to restrain said body against removal from the needle when the protecting device is moved from a position on the needle spaced from the tip to a position where said body encloses the tip; and (c) means carried by said body for prevention of the re-emergence of said needle from said body once the tip of said needle has been withdrawn within said body.

3. A needle tip protecting device as in claim 2 further comprising:

(a) energy storage means connected to said body for actuating said needle engagement means;

(b) retention means for releaseably suspending the actuation of said needle engagement means by said energy storage means; and (c) trigger means operatively associated with said body for sensing the presence or absence of the tip of said needle within said body and releasing said retention means when the tip of said needle is withdrawn into said body thereby allowing said energy storage means to actuate said needle engagement means.

4. A needle tip protecting device as in claim 2 wherein said engagement means comprises:

(i) a locking plate positioned within said body, said locking plate having an opening therethrough, said opening being pierced by said needle with a close, sliding fit;

(ii) alignment means to maintain said opening and said needle is sliding alignment while the needle tip is outside of said body; and (iii) canting means to cant said locking plate into locking engagement with said needle when said tip has entered within said body.

5. A needle tip protecting device as in claims 2, 3 or 1 in combination with a syringe carrying said needle.

6. A needle tip protecting device as in claim 5 further comprising handle means attached to said body, said handle means being disposed rearwardly from said needle in a storage position adjacent to aid syringe.

7. A needle tip protecting device as in claim 4 wherein said canting means comprises energy storage means in the form of a spring means with a first end thereof in contact with said body and with the second end thereof in contact with said locking plate, the stored energy of said spring means being thereby directed to bias said locking plate to be canted on said needle shaft.

8. A needle tip protecting device as in claim 4 or 7 wherein said alignment means comprises a lever arm, with first and second ends, contained within said body, the first end of said lever arm being attached to a first end of said locking plate and the second end of said lever arm being in contact with said needle and aligned so as to prevent canting of said locking plate so long as said needle tip is exterior to said needle body.

9. A needle tip protecting device as in claims 4 or 7 in combination with a syringe carrying said needle.

10. A needle tip protecting device as in claim further comprising handle means attached to said body, said handle means being disposed rearwardly from said needle in a storage position adjacent to said syringe.

11. A needle tip protecting device as in claim 8 wherein the second end of the lever arm comprises a blocking plate which is in contact with the needle while the needle tip is outside the body, said lever-arm being biased by the canting means to rotate in a direction that tends to bring said blocking plate into the path of the needle once the needle has been drawn past the point of being in contact with the blocking plate.

12. A needle tip protecting device as in claim 8 in combination with a syringe carrying said needle.

13. A needle tip protecting device as in claim 12 further comprising handle means attached to said body, said handle means being disposed rearwardly from said needle in a storage position adjacent to said syringe.

14. A needle tip protecting device as in claim 11 in combination with a syringe carrying said needle.

15. A needle tip protecting device as in claim 14 further comprising handle means attached to said body, said handle means being disposed rearwardly from said needle in a storage position adjacent to said syringe.

* * * * *